(12) United States Patent
Gross et al.

(10) Patent No.: US 12,728,004 B1
(45) Date of Patent: Sep. 8, 2026

(54) DEVICE AND METHOD FOR TREATMENT OF DIASTOLIC HEART FAILURE

(71) Applicants: Yossi Gross, Moshav Mazor (IL); Dana Sternik, Savyon (IL)

(72) Inventors: Yossi Gross, Moshav Mazor (IL); Dana Sternik, Savyon (IL)

( * ) Notice: Subject to any disclaimer, the term of this patent is extended or adjusted under 35 U.S.C. 154(b) by 0 days.

(21) Appl. No.: 19/467,090

(22) Filed: Feb. 2, 2026

(51) Int. Cl.
*A61F 2/24* (2006.01)

(52) U.S. Cl.
CPC .... *A61F 2/2487* (2013.01); *A61F 2210/0014* (2013.01); *A61F 2220/0016* (2013.01); *A61F 2230/0091* (2013.01); *A61F 2250/0069* (2013.01)

(58) Field of Classification Search
CPC ............ A61F 2/2487; A61F 2210/0014; A61F 2220/0016; A61F 2230/0091; A61F 2250/0069; A61F 2/2481; A61F 2002/2484; A61F 2002/249; A61F 2/0063; A61B 2017/00243
USPC .............................................................. 600/37
See application file for complete search history.

(56) References Cited

U.S. PATENT DOCUMENTS 6,045,497 A * 4/2000 Schweich, Jr. .. A61B 17/00234 600/16
8,382,653 B2 2/2013 Dubi et al.
8,672,827 B2 3/2014 Nikolic et al.
9,131,928 B2 * 9/2015 Zlotnick ............... A61F 2/2487
11,026,791 B2 * 6/2021 Genovese ............. A61F 2/2463
11,033,392 B2 6/2021 Lichtenstein et al.
11,219,754 B2 1/2022 Gross
11,357,629 B1 6/2022 Gross
11,395,910 B2 7/2022 Gross
(Continued)

FOREIGN PATENT DOCUMENTS

CN 119497601 A * 2/2025 ......... A61B 17/0469
WO 2003007778 A2 1/2003
(Continued)

OTHER PUBLICATIONS

Jonathan Weissmann, et al., "A numerical study of a left ventricular expander for heart failure with preserved ejection fraction, Royal Society Open Science", vol. 10, No. 230142, 2023, pp. 1-14.

*Primary Examiner* — Brian L Casler
(74) *Attorney, Agent, or Firm* — Sughrue Mion, PLLC

(57) ABSTRACT

An implant comprising one or more resilient force-applying elements for exerting a longitudinal force to (1) an atrioventricular fibrous structure and (2) tissue at an apical region of the heart, in order to augment longitudinal motion of an atrioventricular plane of an atrioventricular valve of the heart, is implanted by positioning a caudal end portion of the implant at the tissue at the apical region, and positioning an opposite end portion of the implant that is opposite the caudal end portion, at the atrioventricular fibrous structure. During ventricular systole, the resilient force-applying element stores energy by compressing, and during ventricular diastole, the resilient force-applying element self-expands longitudinally, to longitudinally push against (1) the atrioventricular fibrous structure and (2) the tissue at the apical region in order to augment the longitudinal motion of the atrioventricular plane of the atrioventricular valve. Other embodiments are also described.

22 Claims, 10 Drawing Sheets

(56) References Cited

U.S. PATENT DOCUMENTS

| | | | | |
|---|---|---|---|---|
| 2004/0064014 | A1* | 4/2004 | Melvin | A61F 2/2487 600/37 |
| 2008/0071134 | A1 | 3/2008 | Dubi et al. | |
| 2025/0339273 | A1 | 11/2025 | Berwick et al. | |

FOREIGN PATENT DOCUMENTS

| | | | | |
|---|---|---|---|---|
| WO | 2004066805 | A2 | 8/2004 | |
| WO | 2021234691 | A1 | 11/2021 | |
| WO | 2023073692 | A1 | 5/2023 | |
| WO | WO-2024118313 | A1 * | 6/2024 | A61F 2/2487 |

* cited by examiner

DEVICE AND METHOD FOR TREATMENT OF DIASTOLIC HEART FAILURE

FIELD OF THE INVENTION

Some applications of the present invention relate in general to cardiac implants. More specifically, some applications of the present invention relate to implants for treatment of diastolic heart failure.

BACKGROUND

Heart failure with preserved ejection fraction (HFpEF) is a form of heart failure in which the ejection fraction is normal, however the left ventricle becomes stiff and unable to fill properly. The majority of left ventricular stroke volume is generated by longitudinal shortening causing apical atrioventricular plane displacement during systole. The lack of effective treatments for HFpEF patients remains an unmet need.

SUMMARY OF THE INVENTION

In some applications of the present invention an implantable diastolic enhancement device is configured to restore physiologic ventricular suction and improve diastolic filling in patients having diastolic heart failure, or heart failure with preserved ejection fraction (HFpEF). The implantable diastolic enhancement device is designed to restore physiologic ventricular suction and improve diastolic filling in HFpEF patients.

In healthy subjects, the majority of left ventricular stroke volume is generated by longitudinal elongation causing apical atrioventricular plane displacement (AVPD) in diastole. Patients having diastolic heart failure lose physiological AV plane motion, ventricular filling becomes pressure-dependent, and elevated end diastolic pressure leads to pulmonary congestion. Typically, AV plane displacement is reduced to around 5.6 mm in severe chronic heart failure patients compared to 14.5 mm in healthy subjects.

The inventors hypothesize that since the atrioventricular plane and the associated fibrous valvular structure undergo coordinated longitudinal motion as a single mechanical unit, an implantable diastolic enhancement device comprising one or more resilient force-applying elements for exerting a longitudinal force to (1) an atrioventricular fibrous structure and (2) tissue at an apical region of the heart, will augment longitudinal motion of an atrioventricular plane of an atrioventricular valve of the patient. The implantable diastolic enhancement device acts like a spring in that, during ventricular systole, the resilient force-applying element stores energy by compressing, and during ventricular diastole, the resilient force-applying element self-expands longitudinally, to longitudinally push against (1) the atrioventricular fibrous structure and (2) the tissue at the apical region in order to augment the longitudinal motion of the atrioventricular plane of the atrioventricular valve.

Typically, but not necessarily, the resilient force-applying element comprises an Euler-buckling member.

The implantable diastolic enhancement device is configured to enhance AV plane motion along the base-apex axis, improves diastolic filling through physiological longitudinal motion, and support ventricular function without active pumping. The elongation of the AV plane reduces the pressure in the ventricle during diastole, and the ventricle fills by suction.

There is therefore provided, in accordance with some applications of the invention, a method for improving diastolic function of a ventricle of a heart of a patient, including:

percutaneously implanting within the ventricle an implant including one or more resilient force-applying elements for exerting a longitudinal force to (1) an atrioventricular fibrous structure and (2) tissue at an apical region of the heart, in order to augment longitudinal motion of an atrioventricular plane of an atrioventricular valve of the heart, by:

positioning a caudal end portion of the implant at the tissue at the apical region; and positioning an opposite end portion of the implant that is opposite the caudal end portion, at the atrioventricular fibrous structure, such that:

during ventricular systole, the resilient force-applying element stores energy by compressing, and during ventricular diastole, the resilient force-applying element self-expands longitudinally, to longitudinally push against (1) the atrioventricular fibrous structure and (2) the tissue at the apical region in order to augment the longitudinal motion of the atrioventricular plane of the atrioventricular valve.

In an application, implanting the implant includes implanting the implant such that the resilient force-applying element is in a compressed state at end-ventricular-diastole and in a more compressed state at end-ventricular-systole.

In an application, implanting the implant includes orienting the resilient force-applying element along a ventricular long axis between the apical region and the atrioventricular fibrous structure.

In an application, the resilient force-applying element includes one or more compressive buckling elements selected from the group consisting of: a rod, a wire, a strip, and a helically coiled element.

In an application, the one or more force-applying elements are configured to buckle laterally.

In an application, the resilient force-applying element includes one or more compressive buckling elements selected from the group consisting of: a straight wire, a wire that is curved when unconstrained, a strip, and a helically coiled element.

In an application, positioning the opposite end portion of the implant at the atrioventricular fibrous structure includes positioning the opposite end portion of the implant at one or more tissues selected from the group consisting of: a left fibrous trigone, an aorto-mitral curtain, and a fibrous portion of a mitral annulus.

In an application, the resilient force-applying element includes an Euler-buckling member.

In an application, implanting the implant includes implanting the implant such that the implant does not directly apply radial forces against a wall of the ventricle.

In an application, implanting the implant includes implanting the implant such that the implant does not contact the wall of the ventricle.

In an application, implanting the implant includes implanting the implant such that the implant contacts only the atrioventricular fibrous structure and the tissue at the apical region.

In an application, implanting the implant includes transapically implanting the implant.

In an application:

positioning the caudal end portion of the implant at the tissue at the apical region includes anchoring the caudal end portion to the tissue at the apical region, and positioning the opposite end portion of the implant at the atrioventricular fibrous structure includes anchoring the opposite end portion to the atrioventricular fibrous structure.

In an application, anchoring the opposite end portion to the atrioventricular fibrous structure includes anchoring the opposite end portion to the atrioventricular fibrous structure using a helical anchor.

In an application, anchoring the caudal end portion to the tissue at the apical region includes anchoring the caudal end portion using one or more load-spreading elements.

In an application, each of the one or more load-spreading elements includes a load-spreading disc.

In an application, each of the one or more load-spreading elements includes a braided nitinol mesh configured to convert axial compressive force into circumferential tensile force.

In an application:

percutaneously implanting the implant includes transapically delivering the implant through an apical access point of the heart;

anchoring the caudal end portion to the tissue at the apical region includes anchoring the caudal end portion using first and second load-spreading elements that are mechanically connected by a longitudinally extending connector, and the method further includes:

positioning the first load-spreading element within the ventricle at the apical access point; and positioning the second load-spreading element adjacent epicardial tissue at the apical access point; and anchoring the caudal end portion using the first and second load-spreading elements includes allowing the first and second load-spreading elements to apply compressive forces against tissue therebetween.

In an application, the method further includes positioning a sealing layer caudally to the first load-spreading element.

In an application:

percutaneously implanting the implant includes transapically delivering the implant through an apical access point of the heart;

anchoring the caudal end portion to the tissue at the apical region includes:

positioning the load-spreading element within the ventricle at the apical access point, the load-spreading element being connected to a longitudinal connector;

passing the longitudinal connector through the apical access point; and positioning a locking element adjacent epicardial tissue at the apical access point; and anchoring the caudal end portion to the tissue at the apical region includes:

moving the locking element along the longitudinal connector toward the load-spreading element; and locking the locking element with respect to the longitudinal connector.

In an application, the locking element includes a locking disc.

In an application, the method further includes positioning a sealing layer caudally to the load-spreading element.

There is also provided, in accordance with some applications of the invention, apparatus for improving diastolic function of a ventricle of a heart of a patient, including:

an implant including one or more resilient force-applying elements for exerting a longitudinal force to (1) an atrioventricular fibrous structure and (2) tissue at an apical region of the heart, to augment longitudinal motion of an atrioventricular plane of an atrioventricular valve of the heart, the implant having:

a caudal end portion configured for positioning at the tissue at the apical region; and an opposite end portion that is opposite the caudal end portion, the opposite end portion configured for positioning at the atrioventricular fibrous structure, the resilient force-applying element is configured to store energy by compressing during ventricular systole, and the resilient force-applying element is configured to self-expand longitudinally during ventricular diastole, to longitudinally push against (1) the atrioventricular fibrous structure and (2) the tissue at the apical region in order to augment the longitudinal motion of the atrioventricular plane of the atrioventricular valve.

In an application, the resilient force-applying element includes one or more compressive buckling elements selected from the group consisting of: a rod, a wire, a strip, and a helically coiled element.

In an application, the one or more force-applying elements are configured to buckle laterally.

In an application, the resilient force-applying element includes one or more compressive buckling elements selected from the group consisting of: a straight wire, a wire that is curved when unconstrained, a strip, and a helically coiled element.

In an application, the opposite end portion of the implant is configured to be positioned at one or more tissues selected from the group consisting of: a left fibrous trigone, an aorto-mitral curtain, and a fibrous portion of a mitral annulus.

In an application, the resilient force-applying element includes an Euler-buckling member.

In an application, the resilient force-applying element includes nitinol.

In an application, the resilient force-applying element is shaped so as to define a lateral bulge between a caudal end portion of the resilient force-applying element and an opposite end portion of the resilient force-applying element.

In an application, the lateral bulge of the resilient force-applying element is configured to store energy by compressing during ventricular systole and to self-expand longitudinally during ventricular diastole.

In an application, the implant is configured to not directly apply radial forces to a wall of the ventricle.

In an application, the implant is configured to not contact the wall of the ventricle.

In an application, the implant is configured such that only the caudal end portion and the opposite end portion are configured to facilitate the longitudinal pushing against the atrioventricular fibrous structure and the tissue at the apical region.

In an application, the apparatus further includes a delivery device, and the implant is disposed in a compressed state within the delivery device.

In an application, the delivery device includes a metal cannula configured for transapical delivery of the implant.

In an application, the cannula has an internal diameter of between 2.0 and 2.5 mm.

In an application, the apparatus further includes a caudal end portion anchor coupled to a caudal end portion of the resilient force-applying element, and an opposite end portion anchor coupled to an opposite end portion of the resilient force-applying element.

In an application:

the caudal end portion of the resilient force-applying element is shaped so as to define a caudal end portion ball, the caudal end portion anchor is shaped so as to define a socket to receive the caudal end portion ball and facilitate rotational movement of the caudal end portion ball with respect to the caudal end portion anchor, the opposite end portion of the resilient force-applying element is shaped so as to define an opposite end portion ball, and the caudal end portion anchor is shaped so as to define a socket to receive the opposite end portion ball and facilitate rotational movement of the opposite end portion ball with respect to the opposite end portion anchor.

In an application, the opposite end portion anchor includes a helical anchor.

In an application, the caudal end portion anchor includes one or more load-spreading elements.

In an application, each of the one or more load-spreading elements includes a load-spreading disc.

In an application, each of the one or more load-spreading elements includes a braided nitinol mesh configured to convert axial compressive force into circumferential tensile force.

In an application:

the implant is configured for transapical delivery through an apical access point of the heart, the caudal end portion anchor includes first and second load-spreading elements that are mechanically connected by a longitudinally extending connector, the first load-spreading element is configured for implantation within the ventricle at the apical access point, the second load-spreading element is configured for implantation adjacent epicardial tissue at the apical access point, and the first and second load-spreading elements are configured to assume an unconstrained shape in which the first and second load-spreading elements move toward each other and apply compressive forces against tissue therebetween.

In an application, the apparatus further includes a sealing layer configured for positioning caudally to the first load-spreading element.

In an application:

the implant is configured for transapical delivery through an apical access point of the heart, the caudal end portion anchor includes one of the one or more load-spreading elements, the caudal end portion anchor includes a longitudinal connector coupled to the one of the one or more load-spreading elements, the one of the one or more load-spreading elements is configured for implantation within the ventricle at the apical access point, the longitudinal connector is configured to pass through the apical access point, the caudal end portion anchor includes a locking element movable along the longitudinal connector and positionable against epicardial tissue at the apical access point, and the locking element is lockable with respect to the longitudinal connector.

In an application, the locking element includes a locking disc.

In an application, the apparatus further includes a sealing layer positionable caudally to the one of the one or more load-spreading elements.

There are therefore provided, in accordance with some applications of the invention, the following inventive concepts:

1. Apparatus, comprising:

an implant configured to be implanted in a ventricle of a patient to enhance diastolic function of a heart of the patient, the implant comprising:

a helical spring comprising:

a caudal portion having an unconstrained caudal-portion diameter, the caudal portion having a caudal end section that is configured to be disposed at and apply pressure to tissue at an apex of the heart of the patient; and an opposite portion opposite to the caudal portion and having an unconstrained opposite-portion diameter that is larger than the caudal portion diameter, the opposite portion having an opposite-portion end section that is configured to be disposed at and apply pressure to subvalvular tissue at an atrioventricular valve of the heart of the patient, wherein the helical spring is configured to:

be longitudinally compressed and store energy during systole, and during diastole, displace an atrioventricular plane of the valve and enhance elastic recoil force of the ventricle by longitudinally pushing (1) the opposite-portion end section against the subvalvular tissue and (2) the caudal end section against the tissue at the apex, by the helical spring self-expanding longitudinally during diastole.

2. The apparatus according to inventive concept 1, further comprising:

a delivery tube for delivering the implant; and a rod disposable within the delivery tube and reversibly coupled to the implant, the rod configured to apply torque to the helical spring after one of the portions of the helical spring is anchored to heart tissue to facilitate anchoring of the other one of the portions of the helical spring to heart tissue in a rotationally preloaded state.

3. The apparatus according to inventive concept 1, wherein the helical spring is configured to not directly apply radial force to a wall of the ventricle.

4. The apparatus according to inventive concept 1, wherein the helical spring is dimensioned such that only the opposite-portion end section and the caudal end section of the helical spring are configured to facilitate the longitudinal pushing by contacting tissue of the ventricle.

5. The apparatus according to inventive concept 1, wherein the caudal portion comprises a plurality of caudal-portion coils and the opposite portion comprises a plurality of opposite-portion coils.

6. The apparatus according to inventive concept 1, wherein the opposite portion has a first plurality of coils having the unconstrained opposite-portion diameter, and wherein the caudal portion has a second plurality of coils having the unconstrained caudal-portion diameter.

7. The apparatus according to inventive concept 1, wherein the helical spring tapers in a caudal direction such that the helical spring is conical in shape.

8. The apparatus according to inventive concept 1, wherein a body of the helical spring at the opposite portion has a circular cross-section, and the body of the helical spring at the caudal portion has a non-circular cross-section.

9. The apparatus according to inventive concept 8, wherein the body of the helical spring at the caudal portion has a rectangular cross-section.

10. The apparatus according to inventive concept 1, further comprising an annuloplasty structure configured to be coupled to an atrial surface of the valve, and wherein the opposite portion of the helical spring is couplable to the annuloplasty structure.

11. The apparatus according to inventive concept 1, further comprising an annuloplasty structure configured to be coupled to an atrial surface of the valve, and wherein the opposite portion of the helical spring is coupled to the annuloplasty structure.

12. Apparatus, comprising:

an implant configured to be implanted in a ventricle of a patient to enhance diastolic function of a heart of the patient, the implant comprising:

a helical spring comprising:

a caudal portion having a caudal end section that is configured to be disposed at and apply pressure to tissue at a papillary muscle of the heart of the patient;

an opposite portion opposite to the caudal portion and having an opposite-portion end section that is configured to be disposed at and apply pressure to subvalvular tissue at an atrioventricular valve of the heart of the patient;

a caudal anchor configured to anchor the caudal end section to the tissue at a papillary muscle; and an opposite portion anchor configured to anchor the opposite-portion end section to the subvalvular tissue, wherein the helical spring is configured to:

be longitudinally compressed and store energy during systole, and during diastole, displace an atrioventricular plane of the valve and enhance elastic recoil force of the ventricle by longitudinally pushing (1) the opposite-portion end section against the subvalvular tissue and (2) the caudal end section against the tissue at the papillary muscle, by the helical spring self-expanding longitudinally during diastole.

13. The apparatus according to inventive concept 12, further comprising:

a delivery tube for delivering the implant; and a rod disposable within the delivery tube and reversibly coupled to the implant, the rod configured to apply torque to the helical spring after one of the portions of the helical spring is anchored to heart tissue to facilitate anchoring of the other one of the portions of the helical spring to heart tissue in a rotationally preloaded state.

14. The apparatus according to inventive concept 12, wherein the helical spring is configured to not directly apply radial force to a wall of the ventricle.

15. The apparatus according to inventive concept 12, wherein the helical spring is dimensioned such that only the opposite-portion end section and the caudal end section of the helical spring are configured to facilitate the longitudinal pushing by contacting tissue of the ventricle.

16. The apparatus according to inventive concept 12, further comprising an annuloplasty structure configured to be coupled to an atrial surface of the valve, and wherein the opposite portion of the helical spring is couplable to the annuloplasty structure.

17. The apparatus according to inventive concept 12, further comprising an annuloplasty structure configured to be coupled to an atrial surface of the valve, and wherein the opposite portion of the helical spring is coupled to the annuloplasty structure.

18. Apparatus, comprising:

an implant configured to be implanted in a ventricle of a patient to enhance diastolic function of a heart of the patient, the implant comprising:

a plurality of elongate buckling prongs having caudal ends and opposite ends opposite to the caudal portion ends;

a base configured to be disposed at and apply pressure to tissue at an apex of the heart of the patient, the base being coupled to the caudal ends of the plurality of elongate buckling prongs; and a partial ring coupled to the opposite ends of the plurality of elongate buckling prongs and configured to be disposed at and apply pressure to subvalvular tissue at an atrioventricular valve of the heart of the patient, wherein the plurality of elongate buckling prongs are configured to:

be longitudinally compressed and store energy during systole, and during diastole, displace an atrioventricular plane of the valve and enhance elastic recoil force of the ventricle by longitudinally pushing (1) the partial ring against the subvalvular tissue and (2) the base against the tissue of the apex, by the by the plurality of elongate buckling prongs self-expanding longitudinally during diastole.

19. The apparatus according to inventive concept 18, further comprising:

a delivery tube for delivering the implant; and a rod disposable within the delivery tube and reversibly coupled to the implant, the rod configured to apply torque to the implant after one of the portions of the implant is anchored to heart tissue to facilitate anchoring of the other one of the portions of the implant to heart tissue in a rotationally preloaded state.

20. The apparatus according to inventive concept 18, wherein the base is circular.

21. The apparatus according to inventive concept 18, wherein the base comprises a flat coil spring.

22. The apparatus according to inventive concept 18, wherein the plurality of elongate buckling prongs comprises a plurality of helical Euler buckling springs.

23. The apparatus according to inventive concept 18, wherein each of the plurality of elongate buckling prongs has a rectangular cross-section.

24. The apparatus according to inventive concept 18, wherein each of the plurality of elongate buckling prongs is configured to not directly apply radial force to a wall of the ventricle.

25. The apparatus according to inventive concept 18, wherein the implant is dimensioned such that only the partial ring and the base are configured to facilitate the longitudinal pushing by contacting tissue of the ventricle.

26. The apparatus according to inventive concept 18, further comprising an annuloplasty structure configured to be coupled to an atrial surface of the valve, and wherein the partial ring is couplable to the annuloplasty structure.

27. The apparatus according to inventive concept 18, further comprising an annuloplasty structure configured to be coupled to an atrial surface of the valve, and wherein the partial ring is coupled to the annuloplasty structure.

28. Apparatus, comprising:
an implant configured to be implanted in a ventricle of a patient to enhance diastolic function of a heart of the patient, the implant comprising:
a plurality of elongate buckling prongs having caudal ends and opposite ends opposite to the caudal ends; and
a helical spring having a caudal end section configured to be disposed at and apply pressure to tissue at an apex of the heart of the patient, the helical spring being coupled to the caudal ends of the plurality of elongate buckling prongs;
wherein the plurality of elongate buckling prongs are configured to:
be longitudinally compressed and store energy during systole, and
during diastole, displace an atrioventricular plane of the valve and enhance elastic recoil force of the ventricle by longitudinally pushing (1) the opposite ends of the elongate buckling prongs to apply pressure to the subvalvular tissue and (2) the caudal end of the helical compression spring against the tissue of the apex, by the by the plurality of elongate buckling prongs self-expanding longitudinally during diastole.

29. The apparatus according to inventive concept 28, further comprising a base coupled to the caudal ends of the plurality of elongate buckling prongs.

30. The apparatus according to inventive concept 28, wherein the plurality of elongate buckling prongs are configured to, during diastole, displace the atrioventricular plane of the valve and enhance elastic recoil force of the ventricle by longitudinally pushing the opposite ends against the subvalvular tissue.

31. The apparatus according to inventive concept 28, further comprising a partial ring coupled to the opposite ends of the plurality of elongate buckling prongs and configured to be disposed at and apply pressure to subvalvular tissue at an atrioventricular valve of the heart of the patient, and wherein the plurality of elongate buckling prongs are configured to, during diastole, displace the atrioventricular plane of the valve and enhance elastic recoil force of the ventricle by longitudinally pushing the partial ring against the subvalvular tissue.

32. The apparatus according to inventive concept 31, further comprising an annuloplasty structure configured to be coupled to an atrial surface of the valve, and wherein the partial ring is couplable to the annuloplasty structure.

33. The apparatus according to inventive concept 31, further comprising an annuloplasty structure configured to be coupled to an atrial surface of the valve, and wherein the partial ring is coupled to the annuloplasty structure.

34. The apparatus according to inventive concept 28, further comprising:
a delivery tube for delivering the implant; and
a rod disposable within the delivery tube and reversibly coupled to the implant, the rod configured to apply torque to the implant after one of the portions of the implant is anchored to heart tissue to facilitate anchoring of the other one of the portions of the implant to heart tissue in a rotationally preloaded state.

35. The apparatus according to inventive concept 28, wherein the plurality of elongate buckling prongs comprises a plurality of helical Euler buckling springs.

36. The apparatus according to inventive concept 28, wherein each of the plurality of elongate buckling prongs has a rectangular cross-section.

37. The apparatus according to inventive concept 28, wherein each of the plurality of elongate buckling prongs is configured to not directly apply radial force to a wall of the ventricle.

38. The apparatus according to inventive concept 28, wherein the implant is dimensioned such that only the partial ring and the caudal end section of the helical compression spring are configured to facilitate the longitudinal pushing by contacting tissue of the ventricle.

39. The apparatus according to inventive concept 28, further comprising an annuloplasty structure configured to be coupled to an atrial surface of the valve, and wherein the opposite ends of the plurality of elongate buckling prongs are couplable to the annuloplasty structure.

40. The apparatus according to inventive concept 28, further comprising an annuloplasty structure configured to be coupled to an atrial surface of the valve, and wherein the opposite ends of the plurality of elongate buckling prongs are coupled to the annuloplasty structure.

41. Apparatus, comprising:
an implant configured to be implanted in a ventricle of a patient to enhance diastolic function of a heart of the patient, the implant comprising:
a base configured to be disposed at and apply pressure to tissue at an apex of the heart of the patient; and
a plurality of elongate buckling prongs extending from the base and having caudal ends and opposite ends opposite to the caudal ends, the opposite ends being configured to be disposed at and apply pressure to subvalvular tissue at an atrioventricular valve of the heart of the patient, wherein:
the plurality of elongate buckling prongs are configured to:
be longitudinally compressed and store energy during systole, and
during diastole, displace an atrioventricular plane of the valve and enhance elastic recoil force of the ventricle by longitudinally pushing (1) the opposite ends of the elongate buckling prongs against the subvalvular tissue and (2) the base against the tissue of the apex, by the by the plurality of elongate buckling prongs self-expanding longitudinally during diastole.

42. A method for improving diastolic function of a ventricle of a heart of a patient, comprising:
percutaneously implanting within the ventricle an implant in a rest condition, the implant having a longitudinally-elongating portion for exerting a longitudinal force to (1) subvalvular tissue and (2) one or more tissues selected from the group consisting of: tissue at an apex of the heart and tissue at a papillary muscle of the heart, in order to displace an atrioventricular plane of the valve and enhance elastic recoil force of the ventricle during diastole, by:

positioning a caudal end portion of the implant at the selected tissue; and positioning an opposite end portion of the implant that is opposite the caudal end, at the subvalvular tissue, such that:

during ventricular systole, the longitudinally-elongating portion compresses such that the implant stores energy, and during ventricular diastole, the longitudinally-elongating portion self-expands longitudinally, to longitudinally push against (1) the subvalvular tissue and (2) the selected tissue in order to displace an atrioventricular plane of the valve and enhance elastic recoil force of the ventricle.

43. The method according to inventive concept 42, wherein:

positioning the caudal end portion of the implant at the selected tissue comprises anchoring the caudal end portion to the selected tissue, and positioning the opposite end portion of the implant at the subvalvular tissue comprises anchoring the opposite end portion to the subvalvular tissue.

44. The method according to inventive concept 42, wherein implanting the implant comprises implanting the implant such that the implant contacts only the subvalvular tissue and the selected tissue.

45. The method according to inventive concept 42, wherein implanting the implant comprises implanting the implant such that the does not apply radial forces against a wall of the ventricle.

46. The method according to inventive concept 42, wherein the implanting the implant comprises anchoring of one of the portions of the implant to heart tissue in a rotationally preloaded state by applying torque to the implant after anchoring the other one of the portions of the implant to heart tissue.

The present invention will be more fully understood from the following detailed description of applications thereof, taken together with the drawings, in which:

DETAILED DESCRIPTION OF EMBODIMENTS

Figure 1A:
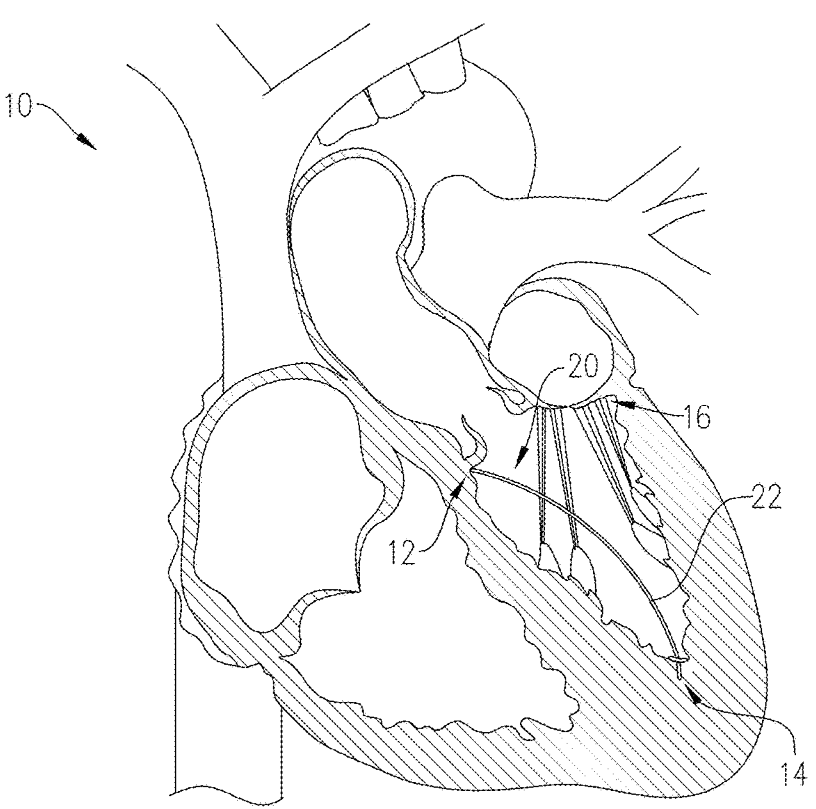
FIGS. 1A-B are schematic illustrations showing perspective views of a mechanical diastolic enhancement device, in accordance with some applications of the invention.
Figure 1B:
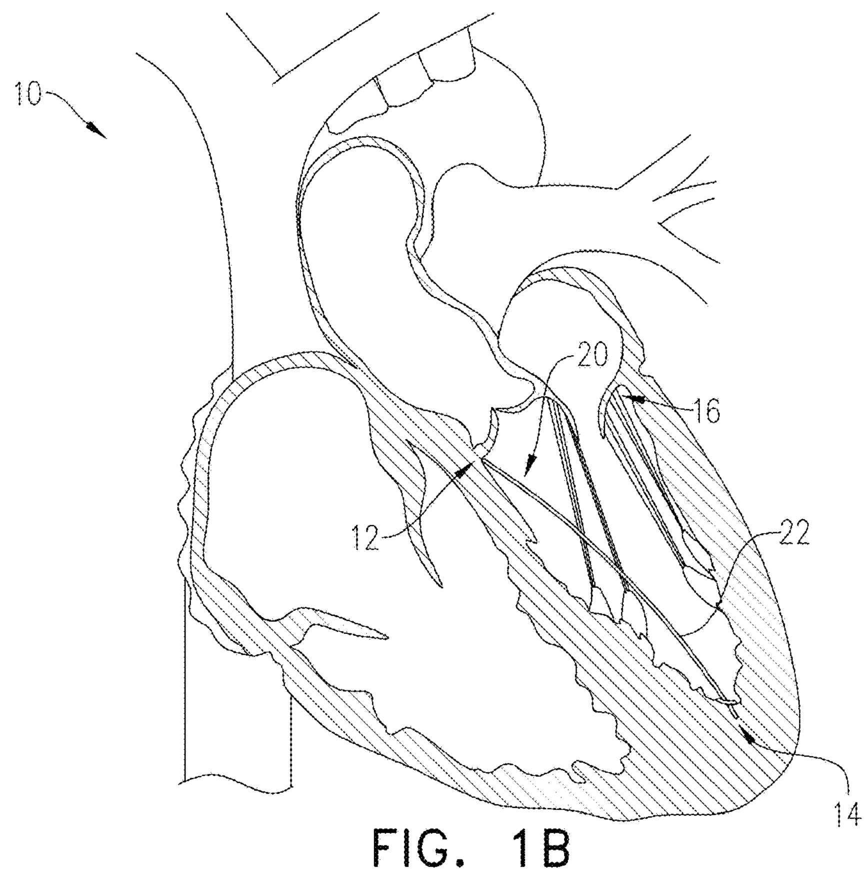

Reference is now made to FIGS. 1A-B, which are schematic illustrations showing perspective views of a mechanical diastolic enhancement device 10, in accordance with some applications of the invention. Device 10 comprises a cardiac assist device implant 20 which comprises one or more resilient force-applying elements 22 that are configured for implantation between an atrioventricular fibrous structure 12 and tissue 14 at an apical region of the heart of a patient. Resilient force-applying element 22 is configured to exert a longitudinal force to (1) atrioventricular fibrous structure 12 and (2) tissue 14 at the apical region of the heart, in order to augment longitudinal motion of an atrioventricular plane 16 of an atrioventricular valve of the heart, by positioning a caudal end portion of implant 20 at tissue 14 at the apical region, and positioning an opposite end portion of the implant that is opposite the caudal end portion, at atrioventricular fibrous structure 12 such that during ventricular systole (shown in FIG. 1A), resilient force-applying element 22 stores energy by compressing, and during ventricular diastole (shown in FIG. 1B), resilient force-applying element 22 self-expands longitudinally, to longitudinally push against (1) atrioventricular fibrous structure 12 and (2) tissue 14 at the apical region in order to augment the longitudinal motion of atrioventricular plane 16 of the atrioventricular valve.

It is to be noted that although implant 20 is shown as only comprising one resilient force-applying element 22, implant 20 may comprise any number of resilient force-applying elements 22.

Implant 20 is implanted such that resilient force-applying element 22 is in a compressed state at end-ventricular-diastole (FIG. 1B) and in a more compressed state at end-ventricular-systole (FIG. 1A). Implant 20 is implanted such that resilient force-applying element 22 is oriented along a ventricular long axis between the apical region and the atrioventricular fibrous structure. Resilient force-applying element 22 comprises one or more compressive buckling elements selected from the group consisting of: a rod, a wire, a strip, and a helically coiled element. For some applications of the present invention resilient force-applying element 22 comprises an Euler-buckling member. Typically, resilient force-applying element 22 is configured to buckle laterally.

Resilient force-applying element 22 comprises one or more compressive buckling elements selected from the group consisting of: a straight wire, a wire that is curved when unconstrained, a strip, and a helically coiled element. Typically, resilient force-applying element 22 comprises nitinol.

Typically, implant 20 is implanted such that implant 20 does not directly apply radial forces against a wall of the ventricle. Typically, implant 20 is implanted such that implant 20 does not contact the wall of the ventricle.

Typically, implant 20 is implanted such that implant 20 contacts only atrioventricular fibrous structure 12 and tissue 14 at the apical region. As shown, atrioventricular fibrous structure 12 comprises a left fibrous trigone. For some applications, atrioventricular fibrous structure 12 comprises an aorto-mitral curtain or a fibrous portion of a mitral annulus. It is to be noted that although implant 20 is shown as being implanted in a left ventricle to enhance atrioventricular plane displacement of the mitral valve, implant 20 may be implanted in a right ventricle to enhance atrioventricular plane displacement of the tricuspid valve.

Typically, implant 20 is configured for transapical delivery into the heart of the patient. It is to be noted that other suitable methods for delivering implant 20 to the heart are within the scope of the present invention. For example, implant 20 may be configured for transfemoral and/or transseptal delivery and/or any other percutaneous delivery into the heart of the patient.

Figure 2A:
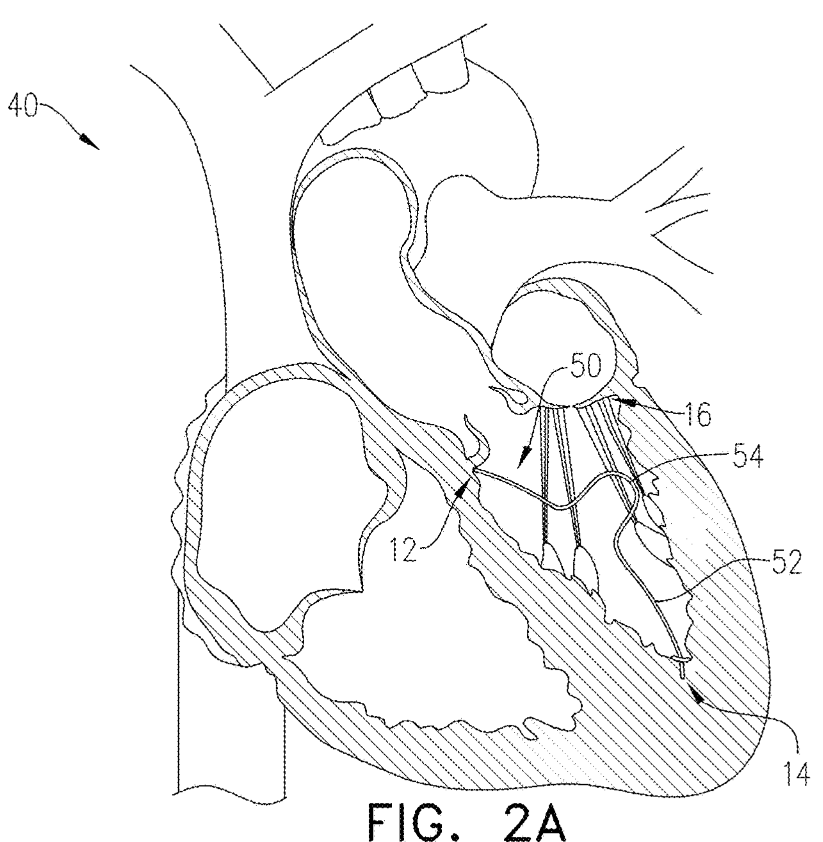
FIGS. 2A-B are schematic illustrations showing perspective views of another mechanical diastolic enhancement device, in accordance with some applications of the invention.
Figure 2B:
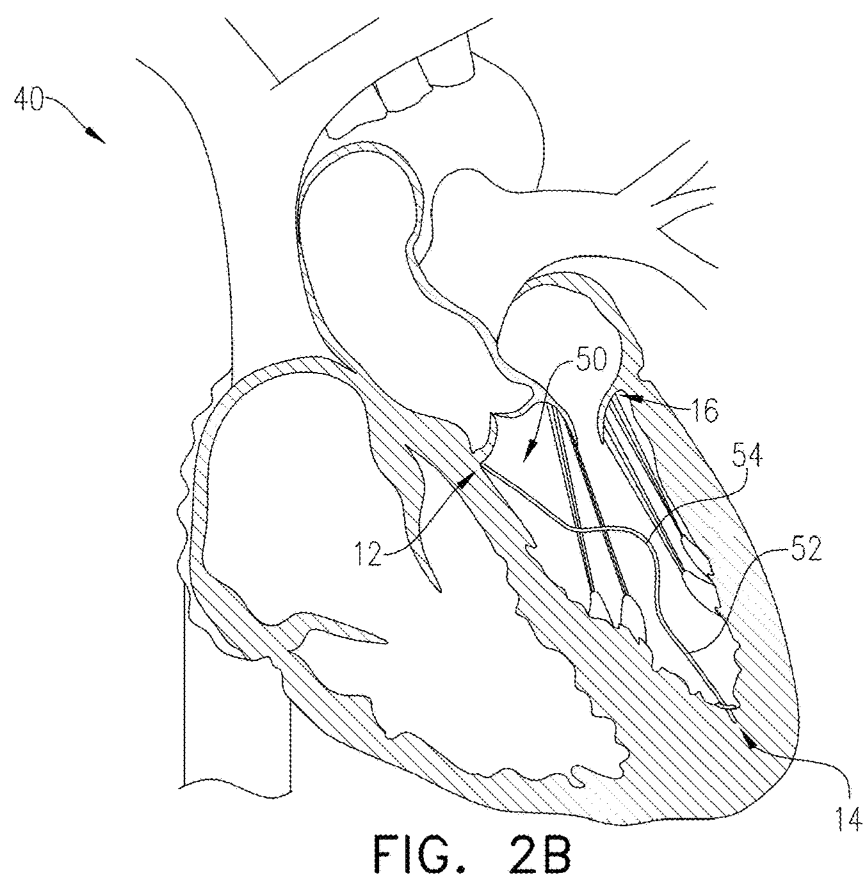

Reference is now made to FIGS. 2A-B, which are schematic illustrations showing perspective views of a mechanical diastolic enhancement device 40, in accordance with some applications of the invention. Device 40 comprises a cardiac assist device implant 50 which comprises one or more resilient force-applying elements 52 that are configured for implantation between an atrioventricular fibrous structure 12 and tissue 14 at an apical region of the heart of a patient. Resilient force-applying element 52 is configured to exert a longitudinal force to (1) atrioventricular fibrous structure 12 and (2) tissue 14 at the apical region of the heart, in order to augment longitudinal motion of an atrioventricular plane 16 of an atrioventricular valve of the heart, by positioning a caudal end portion of implant 50 at tissue 14 at the apical region, and positioning an opposite end portion of the implant that is opposite the caudal end portion, at atrioventricular fibrous structure 12 such that during ventricular systole (shown in FIG. 1A), resilient force-applying element 52 stores energy by compressing, and during ventricular diastole (shown in FIG. 1B), resilient force-applying element 52 self-expands longitudinally, to longitudinally push against (1) atrioventricular fibrous structure 12 and (2) tissue 14 at the apical region in order to augment the longitudinal motion of atrioventricular plane 16 of the atrioventricular valve.

Resilient force-applying element 52 is shaped so as to define a lateral bulge 54 between a caudal end portion of the one or more resilient force-applying elements and an opposite end portion of the one or more resilient force-applying elements. During ventricular systole, as shown in FIG. 2A, bulge 54 is curved in order to compress and store energy, and during ventricular diastole, as shown in FIG. 2B, bulge 54 is less curved and self-expands to provide additional longitudinal force to resilient force-applying element 52.

It is to be noted that although implant 50 is shown as only comprising one resilient force-applying element 52, implant 50 may comprise any number of resilient force-applying elements 52.

Implant 50 is implanted such that resilient force-applying element 52 is in a compressed state at end-ventricular-diastole (FIG. 2B) and in a more compressed state at end-ventricular-systole (FIG. 2A). Implant 50 is implanted such that resilient force-applying element 52 is oriented along a ventricular long axis between the apical region and the atrioventricular fibrous structure. Resilient force-applying element 52 comprises one or more compressive buckling elements selected from the group consisting of: a rod, a wire, a strip, and a helically coiled element. For some applications of the present invention resilient force-applying element 52 comprises an Euler-buckling member. Typically, resilient force-applying element 52 is configured to buckle laterally. Resilient force-applying element 52 comprises one or more compressive buckling elements selected from the group consisting of: a straight wire, a wire that is curved when unconstrained, a strip, and a helically coiled element. Typically, resilient force-applying element 52 comprises nitinol.

Typically, implant 50 is implanted such that implant 50 does not directly apply radial forces against a wall of the ventricle. Typically, implant 50 is implanted such that implant 50 does not contact the wall of the ventricle. Typically, implant 50 is implanted such that implant 50 contacts only atrioventricular fibrous structure 12 and tissue 14 at the apical region. As shown, atrioventricular fibrous structure 12 comprises a left fibrous trigone. For some applications, atrioventricular fibrous structure 12 comprises an aorto-mitral curtain or a fibrous portion of a mitral annulus. It is to be noted that although implant 50 is shown as being implanted in a left ventricle to enhance atrioventricular plane displacement of the mitral valve, implant 50 may be implanted in a right ventricle to enhance atrioventricular plane displacement of the tricuspid valve.

Typically, implant 50 is configured for transapical delivery into the heart of the patient. It is to be noted that other suitable methods for delivering implant 50 to the heart are within the scope of the present invention. For example, implant 50 may be configured for transfemoral and/or transseptal delivery into the heart of the patient.

Reference is now made to FIGS. 3A-B and 5A-C, which are schematic illustrations showing perspective views of a mechanical diastolic enhancement device 60, in accordance with some applications of the invention. Device 60 comprises a cardiac assist device implant 62 which comprises one or more resilient force-applying elements 64 that are configured for implantation between an atrioventricular fibrous structure 12 and tissue 14 at an apical region of the heart of a patient. Resilient force-applying element 64 is configured to exert a longitudinal force to (1) atrioventricular fibrous structure 12 and (2) tissue 14 at the apical region of the heart, in order to augment longitudinal motion of an atrioventricular plane 16 of an atrioventricular valve of the heart, by positioning a caudal end portion of implant 62 at tissue 14 at the apical region, and positioning an opposite end portion of the implant that is opposite the caudal end portion, at atrioventricular fibrous structure 12 such that during ventricular systole (shown in FIG. 5B), resilient force-applying element 64 stores energy by compressing, and during ventricular diastole (shown in FIG. 5C), resilient force-applying element 64 self-expands longitudinally, to longitudinally push against (1) atrioventricular fibrous structure 12 and (2) tissue 14 at the apical region in order to augment the longitudinal motion of atrioventricular plane 16 of the atrioventricular valve.

It is to be noted that although implant 62 is shown as only comprising one resilient force-applying element 64, implant 62 may comprise any number of resilient force-applying elements 64.

Figure 5A:
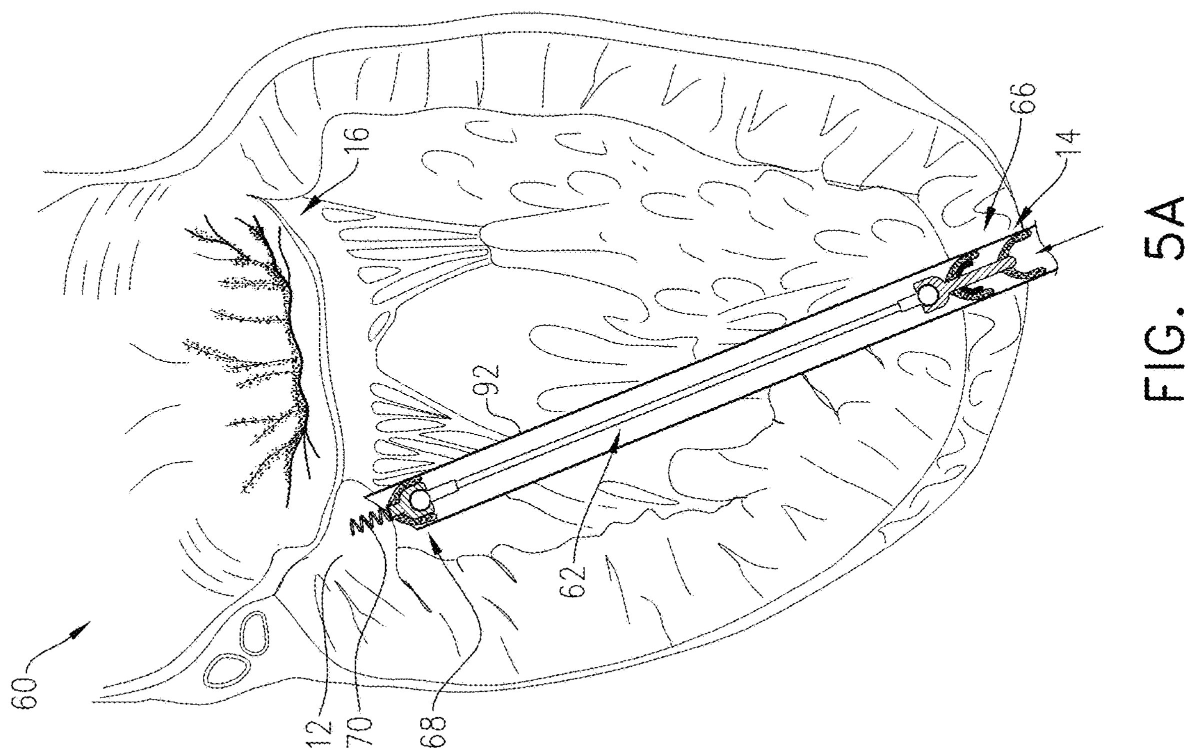
FIGS. 5A-C are schematic illustrations of the implantation of the mechanical diastolic enhancement device of FIGS. 3A-B, in accordance with some applications of the invention.
Figure 5C:
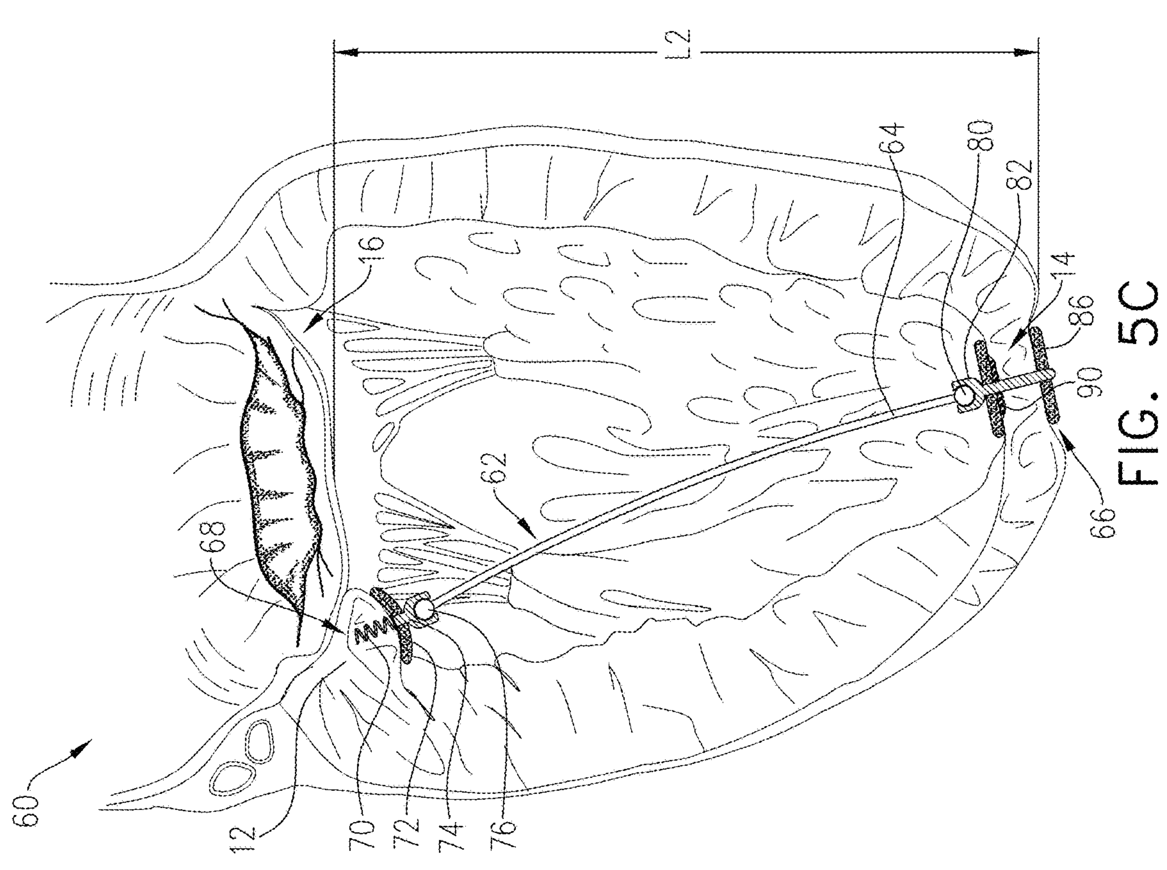
Figure 5B:
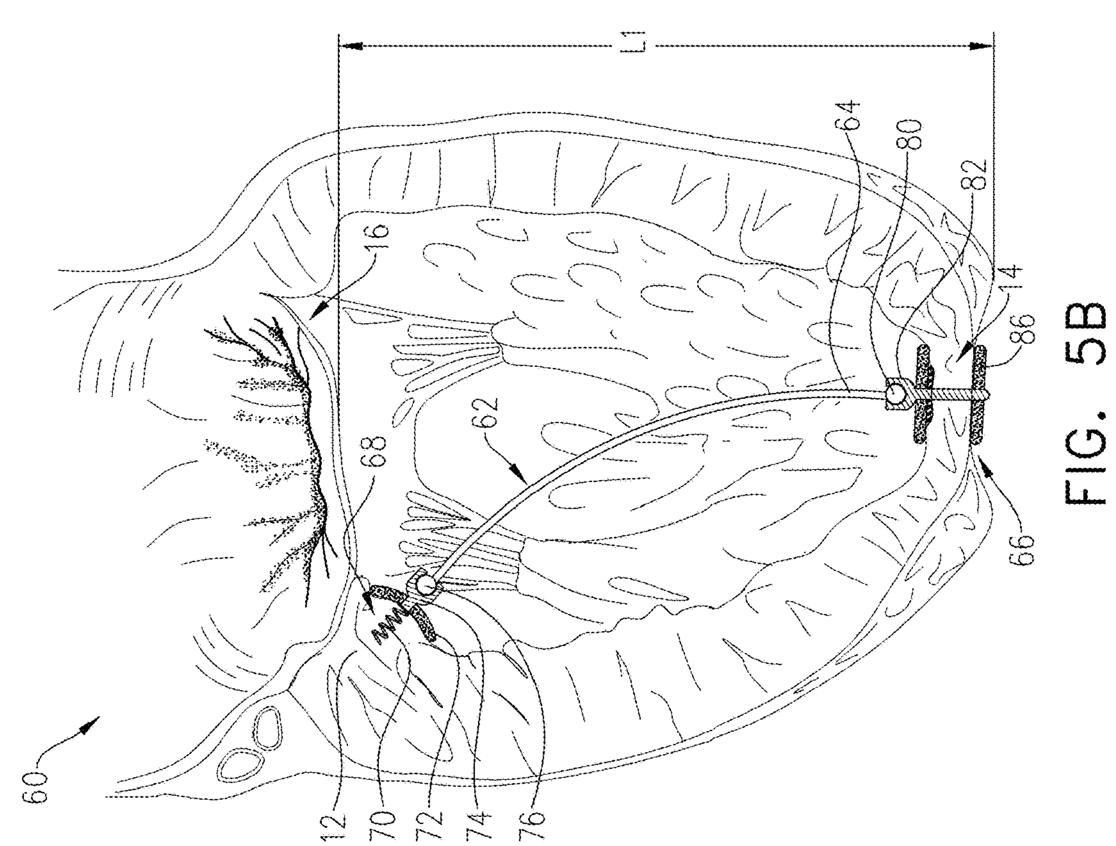

Implant 62 is implanted such that resilient force-applying element 64 is in a compressed state at end-ventricular-diastole (FIG. 5C) and in a more compressed state at end-ventricular-systole (FIG. 5B). Implant 62 is implanted such that resilient force-applying element 64 is oriented along a ventricular long axis between the apical region and the atrioventricular fibrous structure. Resilient force-applying element 64 comprises one or more compressive buckling elements selected from the group consisting of: a rod, a wire, a strip, and a helically coiled element. For some applications of the present invention resilient force-applying element 64 comprises an Euler-buckling member. Typically, resilient force-applying element 64 is configured to buckle laterally. Resilient force-applying element 64 comprises one or more compressive buckling elements selected from the group consisting of: a straight wire, a wire that is curved when unconstrained, a strip, and a helically coiled element. Typically, resilient force-applying element 64 comprises nitinol.

Typically, implant 62 is implanted such that implant 62 does not directly apply radial forces against a wall of the ventricle. Typically, implant 62 is implanted such that implant 62 does not contact the wall of the ventricle. Typically, implant 62 is implanted such that implant 62 contacts only atrioventricular fibrous structure 12 and tissue 14 at the apical region. As shown, atrioventricular fibrous structure 12 comprises a left fibrous trigone. For some applications, atrioventricular fibrous structure 12 comprises an aorto-mitral curtain or a fibrous portion of a mitral annulus. It is to be noted that although implant 62 is shown as being implanted in a left ventricle to enhance atrioventricular plane displacement of the mitral valve, implant 62 may be implanted in a right ventricle to enhance atrioventricular plane displacement of the tricuspid valve.

Typically, implant 62 is configured for transapical delivery into the heart of the patient. It is to be noted that other suitable methods for delivering implant 62 to the heart are within the scope of the present invention. For example, implant 62 may be configured for transfemoral and/or transseptal and/or any other percutaneous delivery into the heart of the patient.

Typically, implant 62 is disposed in a compressed state within a delivery device 92. For some applications, delivery device 92 comprises a metal cannula configured for transapical delivery of implant 62. Typically, the cannula has an internal diameter of between 2.0 and 3.5 mm, e.g., 2.4 mm.

Implant 62 comprises a caudal end portion anchor 66 coupled to a caudal end portion of resilient force-applying element 64, and an opposite end portion anchor 68 coupled to an opposite end portion of resilient force-applying element 64. The caudal end portion resilient force-applying element 64 is shaped so as to define a caudal end portion ball 80 and caudal end portion anchor 66 is shaped so as to define a socket 82 to receive caudal end portion ball 80 and facilitate rotational movement of caudal end portion ball 80 with respect to caudal end portion anchor 66. The opposite end portion of resilient force-applying element 64 is shaped so as to define an opposite end portion ball 76, and opposite end portion anchor 68 is shaped so as to define a socket 74 to receive opposite end portion ball 76 and facilitate rotational movement of opposite end portion ball 76 with respect to opposite end portion anchor 68. As shown, opposite end portion anchor 68 comprises a helical anchor 70 for implantation within atrioventricular fibrous structure 12. Helical anchor 70 has a width of 2.0-3.0 mm, e.g., 2.5 mm and a height of 2-6 mm, e.g., 4 mm. Opposite end portion anchor 68 also comprises one or more load-spreading elements 72, e.g., a load-spreading disc. For some applications, load-spreading element 72 comprises a braided nitinol mesh configured to convert axial compressive force into circumferential tensile force in order to help further anchor opposite end portion anchor 68 to structure 12.

Figure 3A:
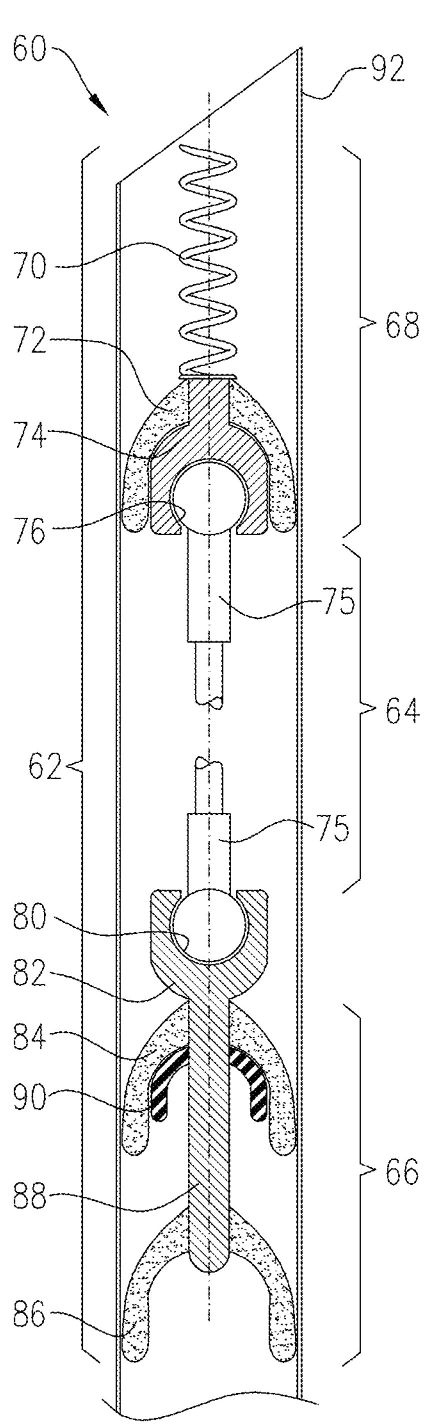
FIGS. 3A-B are schematic illustrations showing perspective views of yet another mechanical diastolic enhancement device, in accordance with some applications of the invention.
Figure 3B:
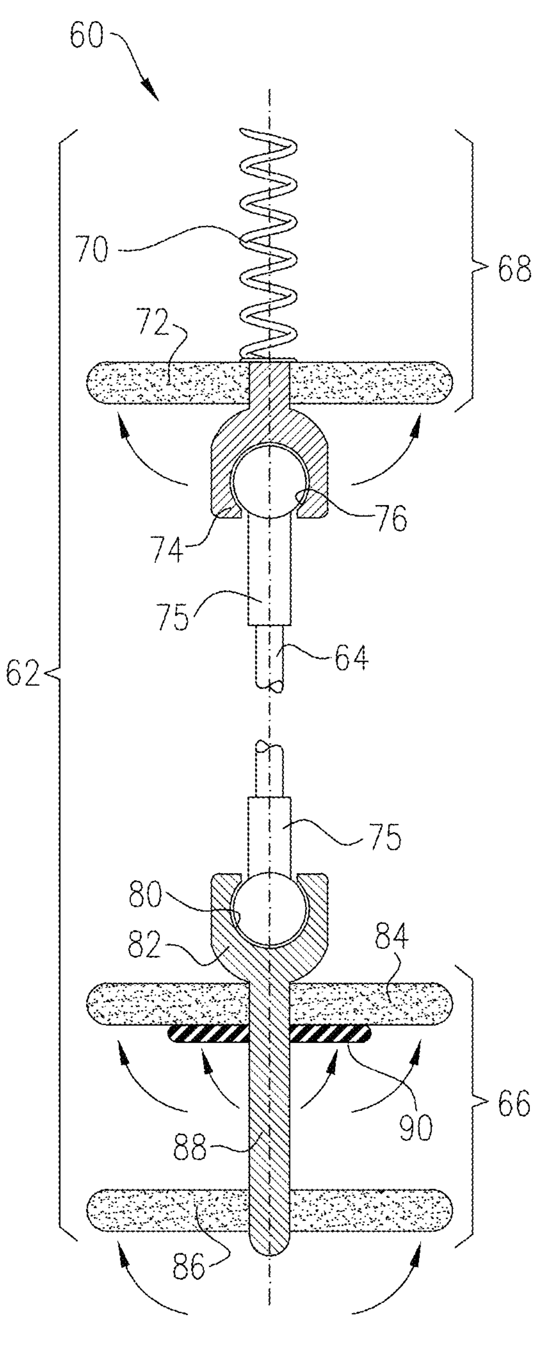

Caudal end portion anchor 66 comprises one or more load-spreading elements, e.g., first and second load-spreading elements 84 and 86. Each load-spreading element 84 and 86 comprises a braided nitinol mesh configured to convert axial compressive force into circumferential tensile force. As shown for example, each of load-spreading elements 84 and 86 comprises a load-spreading disc. Elements 84 and 86 are compressible within a tube of delivery device 92 as shown in FIG. 3A, and is expandable to an expanded state in the absence of the tube of device 92, as shown in FIG. 3B. Elements 84 and 86 form an anchoring assembly employing a double-disc architecture similar to occlude devices for transcatheter delivery. Elements 72, 84, and 86 each have a height of 0.7-1.3 mm e.g., 1 mm, and a width of 5-10 mm, e.g., 7 mm.

Sockets 74 and 82 are each configured as a low-profile ball-and-socket interface defining a pinned boundary condition for resilient force-applying element 64. Sockets 74 and 82 have a height of 2.5-3.0 mm e.g., 2.8 mm. As shown, a strain relief neck 75 extends from each ball 76 and 80 over resilient force-applying element 64. For some applications, neck has a width of 1.0-1.5 mm e.g., 1.2 mm, and a height of 2.5-3.0 mm, e.g., 3.3 mm.

As shown in FIGS. 5A-C, implant 62 is configured for transapical delivery through an apical access point of the heart. First and second load-spreading elements 84 and 86 are mechanically connected by a longitudinally extending connector 88. Connector 88 is fixedly coupled to at least first load-spreading element 84 and/or to second load-spreading element 86. First load-spreading element 84 is configured for implantation within the ventricle at the apical access point, and second load-spreading element 86 is configured for implantation adjacent epicardial tissue at the apical access point. First and second load-spreading elements 84 and 86 are configured to assume an unconstrained shape in which the first and second load-spreading elements move toward each other and apply compressive forces against tissue therebetween. A sealing layer 90 is configured for positioning caudally to first load-spreading element 84. Sealing layer 90 is compressible within the tube of delivery device 92 as shown in FIG. 3A, and is expandable to an expanded state in the absence of the tube of device 92, as shown in FIG. 3B. Sealing layer 90 comprises a polymeric membrane comprising expanded polyterafluoroethylene (ePTFE), polyurethane, and/or a hydrogel material. Typically, ventricular systolic pressure urges sealing layer 90 into contact with surrounding tissue, thereby enhancing hemostatic sealing. Sealing layer 90 has a height of 0.3-0.7 mm, e.g., 0.5 mm, and a width of 3-7 mm e.g., 5 mm. Typically, anchor 66 and socket 82 are configured to bear mechanical loads transmitted from resilient force-applying element 64, while sealing layer 90 is configured to provide sealing without bearing the mechanical loads.

As shown in FIG. 5A, implant 62 is delivered within the heart at a transapical access point and is compressed within a tube of delivery device 92. Device 92 is delivered via a transapical delivery needle under echocardiographic guidance. An apical access point is created, and the needle is withdrawn. Device 92 is advanced until the opposite end portion anchor 68 is disposed at atrioventricular fibrous structure 12. Helical anchor 70 is implanted at atrioventricular fibrous structure 12. As shown in FIG. 5B, device 92 is retracted so as to deploy caudal end portion anchor 66. As device 92 is gradually retracted, load-spreading element 84 and sealing layer 90 expand within the ventricle at the apical access point, longitudinal connector 88 passes through the apical access point, and second load-spreading element 86 expands and applied force against epicardial tissue at the apical access point.

Implant 62 is implanted such that resilient force-applying element 64 is oriented along a ventricular long axis between tissue 14 at the apical region and the atrioventricular fibrous structure 12. Typically, implant 62 is implanted in a manner in which resilient force-applying element 64 is in a compressed state at end-ventricular-diastole and in a more compressed state at end-ventricular-systole. For some applications, implant 62 is implanted such that resilient force-applying element 64 is compressed immediately during delivery and then gets more compressed during systole. For some applications, implant 62 is implanted such that resilient force-applying element 64 is not compressed immediately during delivery and then gets compressed during systole.

As shown in FIG. 5B, at end-ventricular-systole, the ventricle has a length L1 of 55-75 mm, and due to the operation of mechanical diastolic enhancement device 60, at end-ventricular-diastole, the ventricle has a length L2 of 70-90 mm as shown in FIG. 5C. That is, mechanical diastolic enhancement device 60 augments longitudinal motion of atrioventricular plane 16 of the atrioventricular valve of the heart by approximately 10-20 mm, e.g., by approximately 10-15 mm, e.g., by approximately 14 mm, by:

- during ventricular systole, resilient force-applying element 64 stores energy by compressing, and
- during ventricular diastole, resilient force-applying element 64 self-expands longitudinally, to longitudinally push against (1) atrioventricular fibrous structure 12 and (2) tissue 14 at the apical region in order to augment the longitudinal motion of atrioventricular plane 16 of the atrioventricular valve.

Reference is now made to FIGS. 4A-B and 6A-C, which are schematic illustrations showing perspective views of a mechanical diastolic enhancement device 100, in accordance with some applications of the invention. Device 100 comprises a cardiac assist device implant 110 which comprises one or more resilient force-applying elements 64 that are configured for implantation between an atrioventricular fibrous structure 12 and tissue 14 at an apical region of the heart of a patient. Resilient force-applying element 64 is configured to exert a longitudinal force to (1) atrioventricular fibrous structure 12 and (2) tissue 14 at the apical region of the heart, in order to augment longitudinal motion of an atrioventricular plane 16 of an atrioventricular valve of the heart, by positioning a caudal end portion of implant 110 at tissue 14 at the apical region, and positioning an opposite end portion of the implant that is opposite the caudal end portion, at atrioventricular fibrous structure 12 such that during ventricular systole (shown in FIG. 6B), resilient force-applying element 64 stores energy by compressing, and during ventricular diastole (shown in FIG. 6C), resilient force-applying element 64 self-expands longitudinally, to longitudinally push against (1) atrioventricular fibrous structure 12 and (2) tissue 14 at the apical region in order to augment the longitudinal motion of atrioventricular plane 16 of the atrioventricular valve.

It is to be noted that although implant 110 is shown as only comprising one resilient force-applying element 64, implant 110 may comprise any number of resilient force-applying elements 64.

Figure 6A:
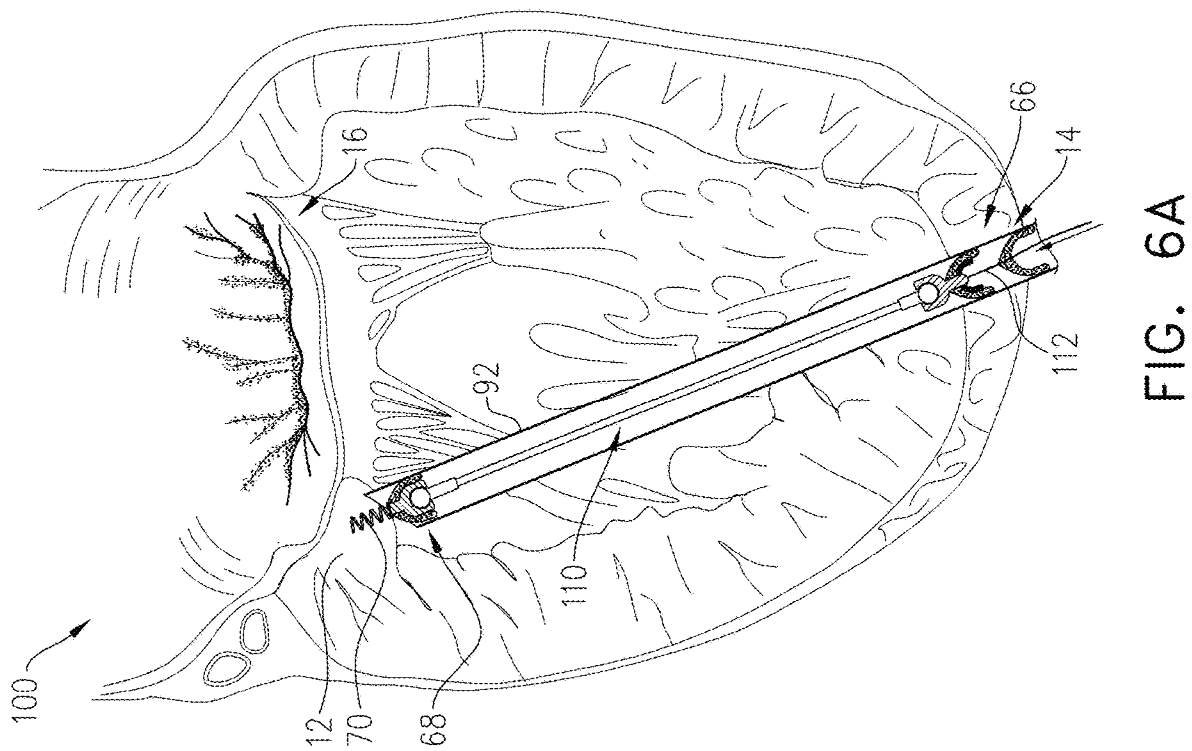
FIGS. 6A-C are schematic illustrations of the implantation of the mechanical diastolic enhancement device of FIGS. 4A-B, in accordance with some applications of the invention.
Figures 6B, 6C:
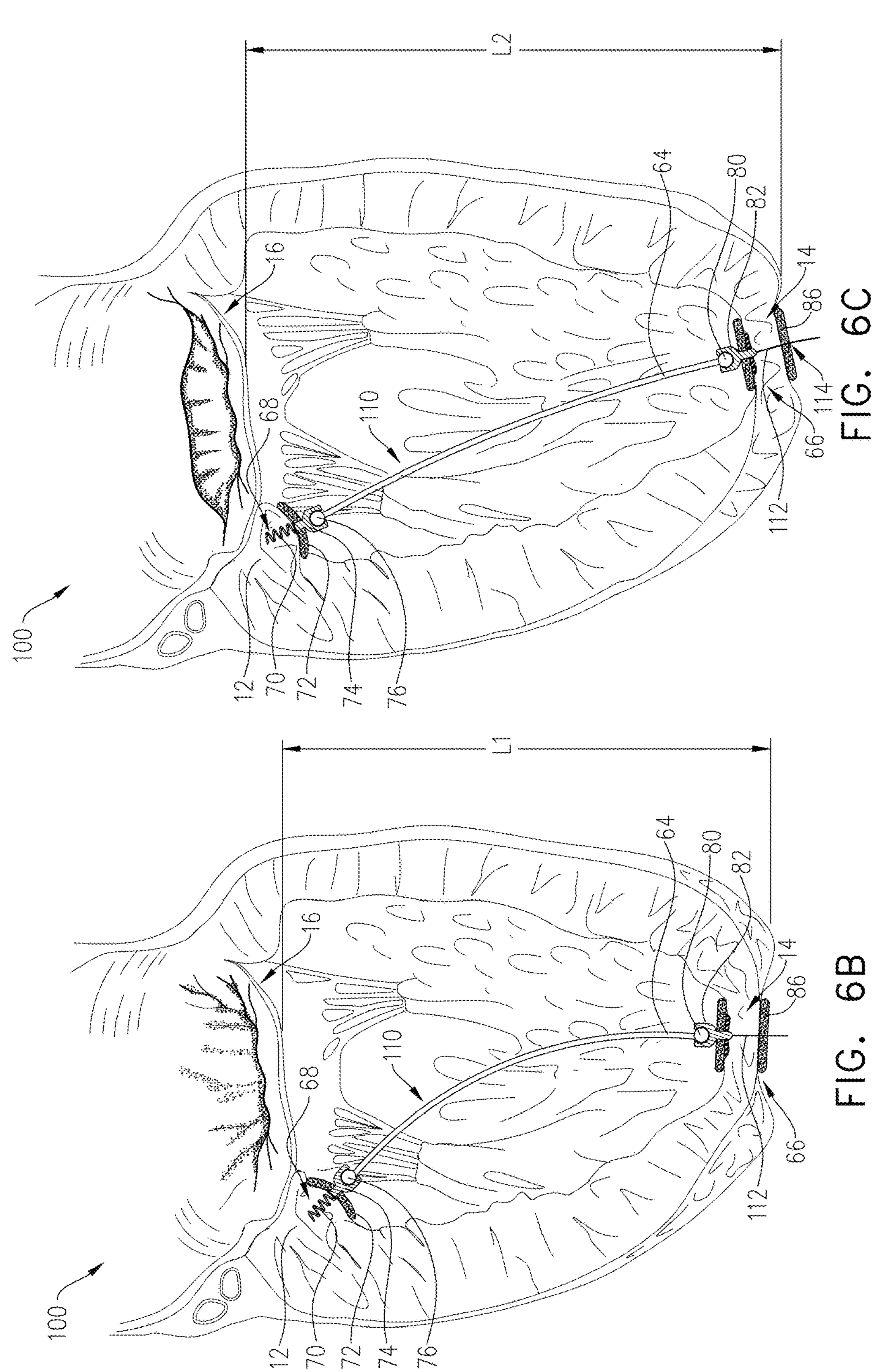

Implant 110 is implanted such that resilient force-applying element 64 is in a compressed state at end-ventricular-diastole (FIG. 6C) and in a more compressed state at end-ventricular-systole (FIG. 6B). Implant 110 is implanted such that resilient force-applying element 64 is oriented along a ventricular long axis between the apical region and the atrioventricular fibrous structure. Resilient force-applying element 64 comprises one or more compressive buckling elements selected from the group consisting of: a rod, a wire, a strip, and a helically coiled element. For some applications of the present invention resilient force-applying element 64 comprises an Euler-buckling member. Typically, resilient force-applying element 64 is configured to buckle laterally. Resilient force-applying element 64 comprises one or more compressive buckling elements selected from the group consisting of: a straight wire, a wire that is curved when unconstrained, a strip, and a helically coiled element. Typically, resilient force-applying element 64 comprises nitinol.

Typically, implant 110 is implanted such that implant 110 does not directly apply radial forces against a wall of the ventricle. Typically, implant 110 is implanted such that implant 110 does not contact the wall of the ventricle. Typically, implant 110 is implanted such that implant 110 contacts only atrioventricular fibrous structure 12 and tissue 14 at the apical region. As shown, atrioventricular fibrous structure 12 comprises a left fibrous trigone. For some applications, atrioventricular fibrous structure 12 comprises an aorto-mitral curtain or a fibrous portion of a mitral annulus. It is to be noted that although implant 110 is shown as being implanted in a left ventricle to enhance atrioventricular plane displacement of the mitral valve, implant 110 may be implanted in a right ventricle to enhance atrioventricular plane displacement of the tricuspid valve.

Typically, implant 110 is configured for transapical delivery into the heart of the patient. It is to be noted that other suitable methods for delivering implant 110 to the heart are within the scope of the present invention. For example, implant 110 may be configured for transfemoral and/or transseptal and/or any other percutaneous delivery into the heart of the patient.

Typically, implant 110 is disposed in a compressed state within a delivery device 92. For some applications, delivery device 92 comprises a metal cannula configured for transapical delivery of implant 110. Typically, the cannula has an internal diameter of between 2.0 and 3.5 mm, e.g., 2.4 mm.

Implant 110 comprises a caudal end portion anchor 66 coupled to a caudal end portion of resilient force-applying element 64, and an opposite end portion anchor 68 coupled to an opposite end portion of resilient force-applying element 64. The caudal end portion resilient force-applying element 64 is shaped so as to define a caudal end portion ball 80 and caudal end portion anchor 66 is shaped so as to define a socket 82 to receive caudal end portion ball 80 and facilitate rotational movement of caudal end portion ball 80 with respect to caudal end portion anchor 66. The opposite end portion of resilient force-applying element 64 is shaped so as to define an opposite end portion ball 76, and opposite end portion anchor 68 is shaped so as to define a socket 74 to receive opposite end portion ball 76 and facilitate rotational movement of opposite end portion ball 76 with respect to opposite end portion anchor 68. As shown, opposite end portion anchor 68 comprises a helical anchor 70 for implantation within atrioventricular fibrous structure 12. Helical anchor 70 has a width of 2.0-3.0 mm, e.g., 2.5 mm and a height of 2-6 mm, e.g., 4 mm. Opposite end portion anchor 68 also comprises one or more load-spreading elements 72, e.g., a load-spreading disc. For some applications, load-spreading element 72 comprises a braided nitinol mesh configured to convert axial compressive force into circumferential tensile force in order to help further anchor opposite end portion anchor 68 to structure 12.

Figures 4A, 4B:
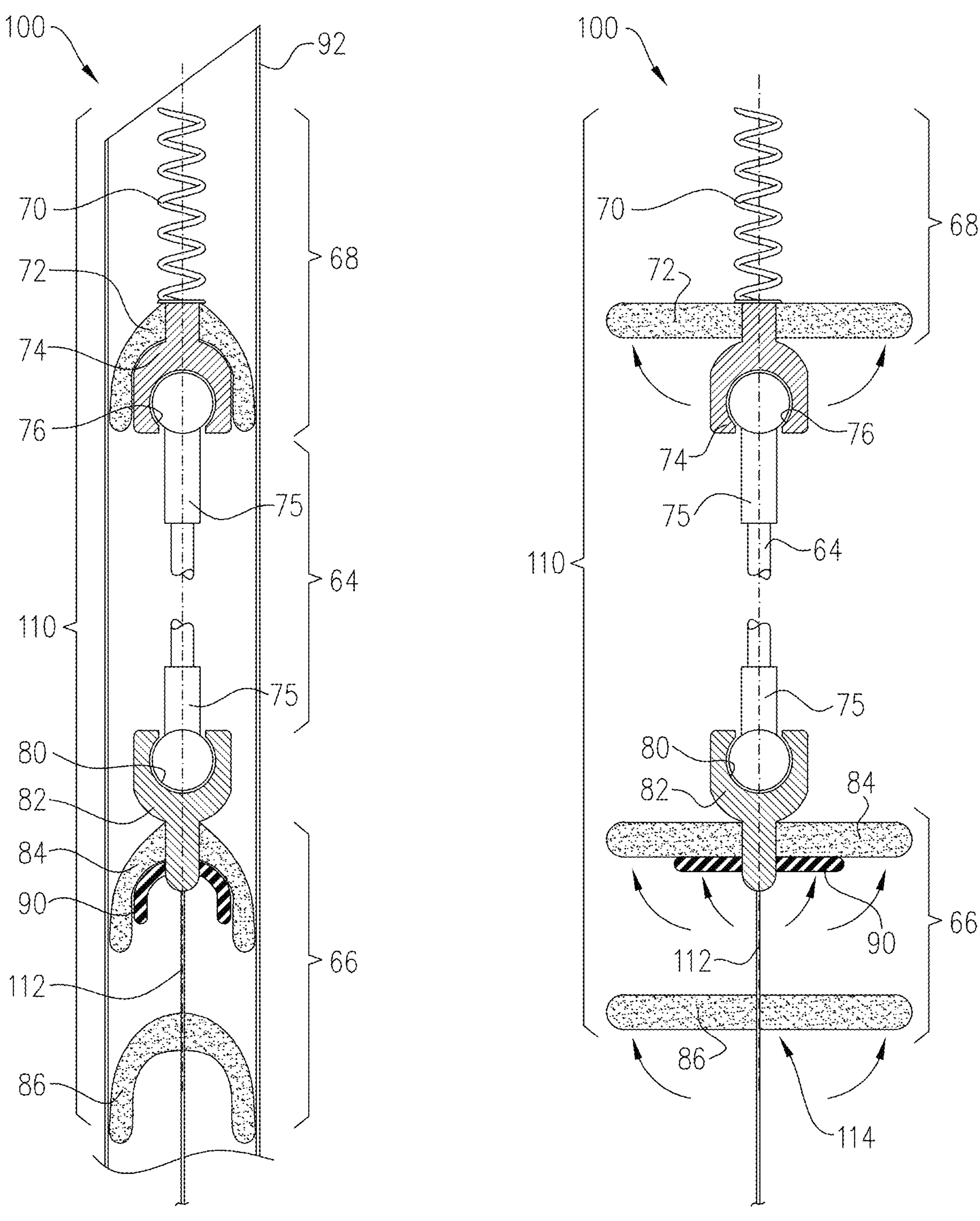
FIGS. 4A-B are schematic illustrations showing perspective views of still another mechanical diastolic enhancement device, in accordance with some applications of the invention.

Caudal end portion anchor 66 comprises one or more load-spreading elements, e.g., first and second load-spreading elements 84 and 86. Each load-spreading element 84 and 86 comprises a braided nitinol mesh configured to convert axial compressive force into circumferential tensile force. As shown for example, each of load-spreading elements 84 and 86 comprises a load-spreading disc. Elements 84 and 86 are compressible within a tube of delivery device 92 as shown in FIG. 4A, and is expandable to an expanded state in the absence of the tube of device 92, as shown in FIG. 4B. Elements 72, 84, and 86 each have a height of 0.7-1.3 mm e.g., 1 mm, and a width of 5-10 mm, e.g., 7 mm.

Sockets 74 and 82 are each configured as a low-profile ball-and-socket interface defining a pinned boundary condition for resilient force-applying element 64. Sockets 74 and 82 have a height of 2.5-3.0 mm e.g., 2.8 mm. As shown, a strain relief neck 75 extends from each ball 76 and 80 over resilient force-applying element 64. For some applications, neck has a width of 1.0-1.5 mm e.g., 1.2 mm, and a height of 2.5-3.0 mm, e.g., 3.3 mm.

As shown in FIGS. 6A-C, implant 110 is configured for transapical delivery through an apical access point of the heart. First and second load-spreading elements 84 and 86 are mechanically connected by a longitudinal connector 112, e.g., a low-profile medical thread, rod, or wire. Connector 112 is fixedly coupled to at least first load-spreading element 84. First load-spreading element 84 is configured for implantation within the ventricle at the apical access point, and second load-spreading element 86 is configured for implantation adjacent epicardial tissue at the apical access point. Second load-spreading element 86 defines or comprises a locking element 114 movable along longitudinal connector 112 and positionable against epicardial tissue at the apical access point. Locking element 114 is lockable with respect to the longitudinal connector 112. For example, locking element 114 comprises a locking disc. For example, locking element 114 comprises a ratchet. First and second load-spreading elements 84 and 86 are configured to assume an unconstrained shape in which the first and second load-spreading elements move toward each other and apply compressive forces against tissue therebetween. A sealing layer 90 is configured for positioning caudally to first load-spreading element 84. Sealing layer 90 is compressible within the tube of delivery device 92 as shown in FIG. 4A, and is expandable to an expanded state in the absence of the tube of device 92, as shown in FIG. 4B. Sealing layer 90 comprises a polymeric membrane comprising expanded polyterafluoroethylene (ePTFE), polyurethane, and/or a hydrogel material. Typically, ventricular systolic pressure urges sealing layer 90 into contact with surrounding tissue, thereby enhancing hemostatic sealing. Sealing layer 90 has a height of 0.3-0.7 mm, e.g., 0.5 mm, and a width of 3-7 mm e.g., 5 mm. Typically, anchor 66 and socket 82 are configured to bear mechanical loads transmitted from resilient force-applying element 64, while sealing layer 90 is configured to provide sealing without bearing the mechanical loads.

As shown in FIG. 6A, implant 110 is delivered within the heart at a transapical access point and is compressed within a tube of delivery device 92. Device 92 is delivered via a transapical delivery needle under echocardiographic guidance. An apical access point is created, and the needle is withdrawn. Device 92 is advanced until the opposite end portion anchor 68 is disposed at atrioventricular fibrous structure 12. Helical anchor 70 is implanted at atrioventricular fibrous structure 12. As shown in FIG. 6B, device 92 is retracted so as to deploy caudal end portion anchor 66. As device 92 is gradually retracted, load-spreading element 84 and sealing layer 90 expand within the ventricle at the apical access point, longitudinal connector 112 passes through the apical access point, and second load-spreading element 86 expands and is pushed along connector toward first load-spreading element 84 such that second load-spreading element 86 applies force against epicardial tissue at the apical access point and is then locked in place by locking element 114.

Implant 110 is implanted such that resilient force-applying element 64 is oriented along a ventricular long axis between tissue 14 at the apical region and the atrioventricular fibrous structure 12. Typically, implant 110 is implanted in a manner in which resilient force-applying element 64 is in a compressed state at end-ventricular-diastole and in a more compressed state at end-ventricular-systole. For some applications, implant 110 is implanted such that resilient force-applying element 64 is compressed immediately during delivery and then gets more compressed during systole. For some applications, implant 110 is implanted such that resilient force-applying element 64 is not compressed immediately during delivery and then gets compressed during systole.

As shown in FIG. 6B, at end-ventricular-systole, the ventricle has a length L1 of 55-75 mm, and due to the operation of mechanical diastolic enhancement device 100, at end-ventricular-diastole, the ventricle has a length L2 of 70-90 mm as shown in FIG. 6C. That is, mechanical diastolic enhancement device 100 augments longitudinal motion of atrioventricular plane 16 of the atrioventricular valve of the heart by approximately 10-20 mm, e.g., by approximately 10-15 mm, e.g., by approximately 14 mm, by:

during ventricular systole, resilient force-applying element 64 stores energy by compressing, and during ventricular diastole, resilient force-applying element 64 self-expands longitudinally, to longitudinally push against (1) atrioventricular fibrous structure 12 and (2) tissue 14 at the apical region in order to augment the longitudinal motion of atrioventricular plane 16 of the atrioventricular valve.

Figure 7:
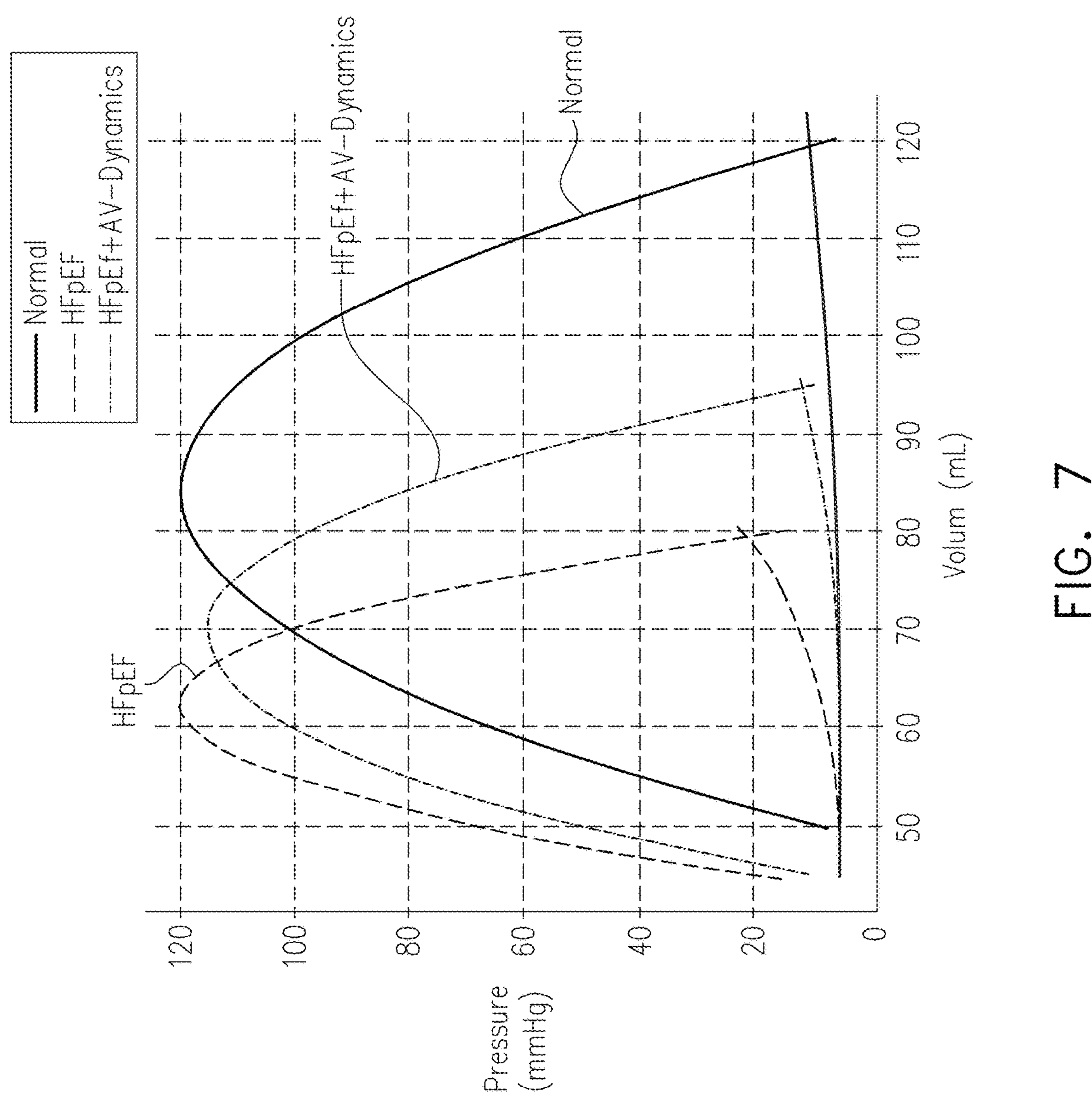
FIG. 7 is a graph representing the left ventricular pressure-volume loops with and without the mechanical diastolic enhancement devices described herein, in accordance with some applications of the present invention.

FIG. 7 is a graph representing the left ventricular pressure-volume loops with and without mechanical diastolic enhancement devices 10, 40, 60, and 100 described herein described herein, in accordance with some applications of the present invention. The graph shows the pressure loop of a normal subject compared with (1) a patient having heart failure with preserved ejection fraction (HFpEF), and (2) heart failure with preserved ejection fraction (HFpEF) in addition to the mechanical diastolic enhancement devices 10, 40, 60, and 100 described herein (HFpEF+AV-Dynamics). As shown, mechanical diastolic enhancement devices 10, 40, 60, and 100 described herein improve the pressure loop of patients having heart failure with preserved ejection fraction (HFpEF).

Figure 8A:
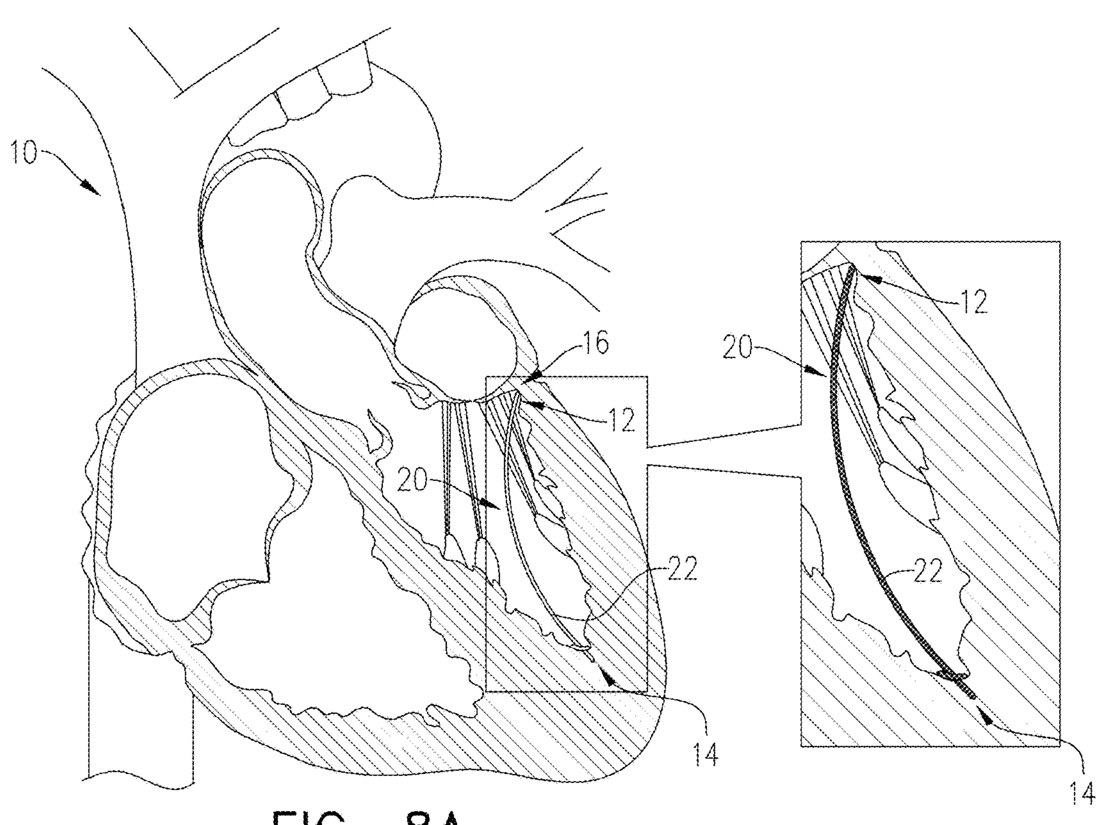
FIGS. 8A-B are schematic illustrations of the implantation of the mechanical diastolic enhancement device of FIGS. 1A-B in a different orientation, in accordance with some applications of the invention.
Figure 8B:
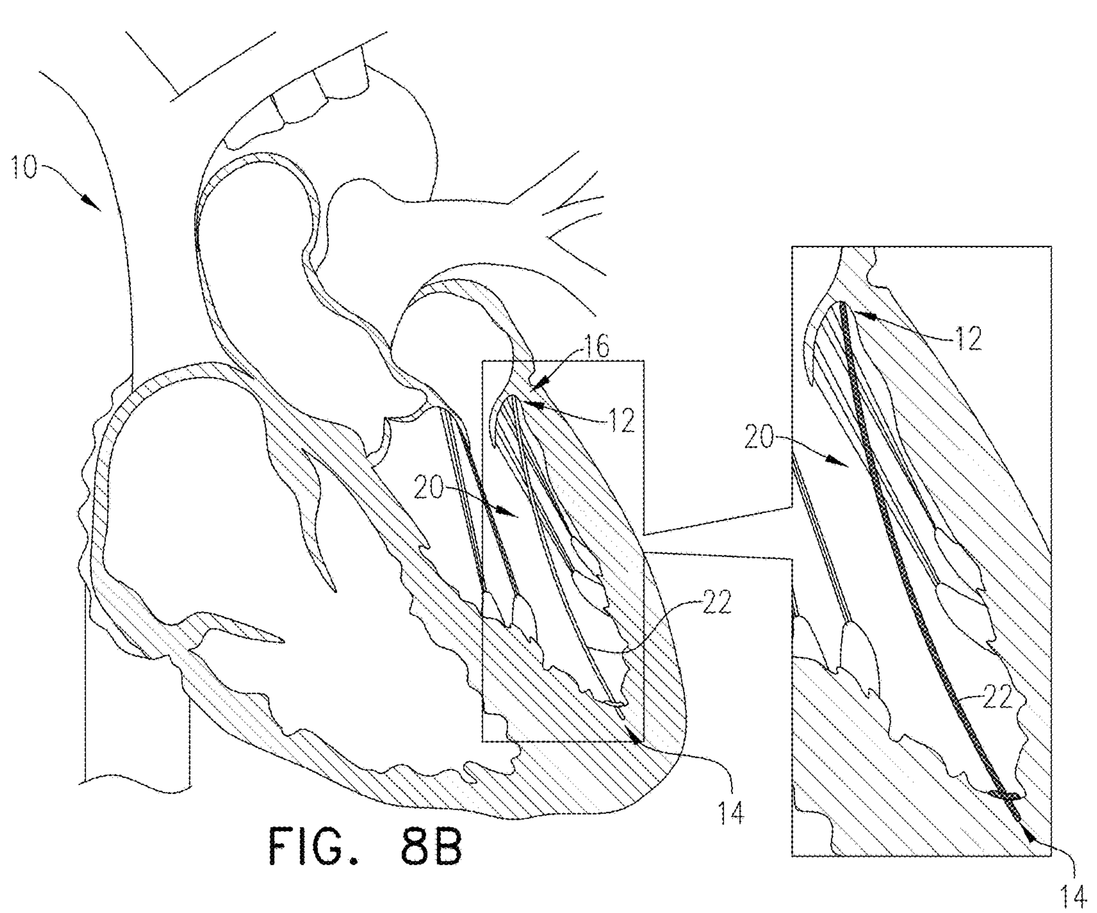

FIGS. 8A-B are schematic illustrations of the implantation of mechanical diastolic enhancement device 10 of FIGS. 1A-B in a different orientation, in accordance with some applications of the invention.

Reference is now made to FIGS. 1A-B, 2A-B, 3A-B, 4A-B, 5A-C, 6A-C, and 8A-B. In healthy subjects, the majority of left ventricular stroke volume is generated by longitudinal elongation causing apical atrioventricular plane displacement (AVPD) in diastole. Patients having diastolic heart failure lose physiological AV plane motion, ventricular filling becomes pressure-dependent, and elevated end diastolic pressure leads to pulmonary congestion. Typically, AV plane displacement is reduced to around 5.6 mm in severe chronic heart failure patients compared to 14.5 mm in healthy subjects.

The inventors hypothesize that since the atrioventricular plane and the associated fibrous valvular structure undergo coordinated longitudinal motion as a single mechanical unit, an implantable diastolic enhancement devices 10, 40, 60, and 100 described herein comprising a resilient force-applying element 22 and 64 for exerting a longitudinal force to (1) an atrioventricular fibrous structure and (2) tissue at an apical region of the heart, will augment longitudinal motion of an atrioventricular plane of an atrioventricular valve of the patient. The implantable diastolic enhancement device acts like a spring in that, during ventricular systole, the resilient force-applying element stores energy by compressing, and during ventricular diastole, the resilient force-applying element self-expands longitudinally, to longitudinally push against (1) the atrioventricular fibrous structure and (2) the tissue at the apical region in order to augment the longitudinal motion of the atrioventricular plane of the atrioventricular valve.

For some applications of the present invention, resilient-force applying elements 22, 52, and 64 comprise a smooth, straight wire, strip, or rod having a width of 0.3-1.0 mm, e.g., 0.6 mm and a longitudinal length of 50-150 mm, e.g., 100 mm. For some applications, resilient-force applying elements 22, 52, and 64 comprise a helical spring coil configured to bend laterally. Typically, resilient-force applying elements 22, 52, and 64 comprise a superelastic alloy, e.g., nitinol. For some applications, resilient-force applying elements 22, 52, and 64 comprise a flexible stainless steel. Resilient-force applying elements 22, 52, and 64 apply a substantially constant force over a defined displacement range. Resilient-force applying elements 22, 52, and 64 are configured to not interfere with blood flow dynamics in the ventricle and are configured to not interfere with the chordae tendinea. Typically, resilient-force applying elements 22, 52, and 64 is configured to apply around 100-300 grams, e.g., 150 grams or 250 grams, of force to atrioventricular fibrous structure 12 and tissue 14 at an apical region of the heart.

The implantable diastolic enhancement devices 10, 40, 60, and 100 described herein are configured to enhance AV plane motion along the base-apex axis, improves diastolic filling through physiological longitudinal motion, and support ventricular function without active pumping. The elongation of the AV plane reduces the pressure in the ventricle during diastole, and the ventricle fills by suction.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for improving diastolic function of a ventricle of a heart of a patient, comprising:

percutaneously implanting within the ventricle an implant comprising one or more resilient force-applying elements for exerting a longitudinal force to (1) an atrioventricular fibrous structure and (2) tissue at an apical region of the heart, in order to augment longitudinal motion of an atrioventricular plane of an atrioventricular valve of the heart, by:

positioning a caudal end portion of the implant at the tissue at the apical region; and positioning an opposite end portion of the implant that is opposite the caudal end portion, at the atrioventricular fibrous structure, such that:

during ventricular systole, the one or more resilient force-applying elements stores energy by compressing, and during ventricular diastole, the one or more resilient force-applying elements self-expand longitudinally, to longitudinally push against (1) the atrioventricular fibrous structure and (2) the tissue at the apical region in order to augment the longitudinal motion of the atrioventricular plane of the atrioventricular valve.

2. The method according to claim 1, wherein implanting the implant comprises implanting the implant such that the one or more resilient force-applying elements are in a compressed state at end-ventricular-diastole and in a more compressed state at end-ventricular-systole.

3. The method according to claim 1, wherein implanting the implant comprises orienting the one or more resilient force-applying elements along a ventricular long axis between the apical region and the atrioventricular fibrous structure.

4. The method according to claim 1, wherein each of the one or more resilient force-applying elements comprise one or more compressive buckling elements selected from the group consisting of: a rod, a wire, a strip, and a helically coiled element.

5. The method according to claim 4, wherein the one or more resilient force-applying elements are configured to buckle laterally.

6. The method according to claim 1, wherein the one or more resilient force-applying elements comprise one or more compressive buckling elements selected from the group consisting of: a straight wire, a wire that is curved when unconstrained, a strip, and a helically coiled element.

7. The method according to claim 1, wherein positioning the opposite end portion of the implant at the atrioventricular fibrous structure comprises positioning the opposite end portion of the implant at one or more tissues selected from the group consisting of: a left fibrous trigone, an aorto-mitral curtain, and a fibrous portion of a mitral annulus.

8. The method according to claim 1, wherein each of the one or more resilient force-applying elements comprise a respective Euler-buckling member.

9. The method according to claim 1, wherein implanting the implant comprises implanting the implant such that the implant does not directly apply radial forces against a wall of the ventricle.

10. The method according to claim 9, wherein implanting the implant comprises implanting the implant such that the implant does not contact the wall of the ventricle.

11. The method according to claim 10, wherein implanting the implant comprises implanting the implant such that the implant contacts only the atrioventricular fibrous structure and the tissue at the apical region.

12. The method according to claim 1, wherein implanting the implant comprises transapically implanting the implant.

13. The method according to claim 1, wherein:

positioning the caudal end portion of the implant at the tissue at the apical region comprises anchoring the caudal end portion to the tissue at the apical region, and positioning the opposite end portion of the implant at the atrioventricular fibrous structure comprises anchoring the opposite end portion to the atrioventricular fibrous structure.

14. The method according to claim 13, wherein anchoring the opposite end portion to the atrioventricular fibrous structure comprises anchoring the opposite end portion to the atrioventricular fibrous structure using a helical anchor.

15. The method according to claim 13, wherein anchoring the caudal end portion to the tissue at the apical region comprises anchoring the caudal end portion using one or more load-spreading elements.

16. The method according to claim 15, wherein each of the one or more load-spreading elements comprises a load-spreading disc.

17. The method according to claim 15, wherein each of the one or more load-spreading elements comprises a braided nitinol mesh configured to convert axial compressive force into circumferential tensile force.

18. The method according to claim 15, wherein:

percutaneously implanting the implant comprises transapically delivering the implant through an apical access point of the heart;

anchoring the caudal end portion to the tissue at the apical region comprises anchoring the caudal end portion using first and second load-spreading elements that are mechanically connected by a longitudinally extending connector, wherein the method further comprises:

positioning the first load-spreading element within the ventricle at the apical access point; and positioning the second load-spreading element adjacent epicardial tissue at the apical access point; and anchoring the caudal end portion using the first and second load-spreading elements comprises allowing the first and second load-spreading elements to apply compressive forces against tissue therebetween.

19. The method according to claim 18, further comprising positioning a sealing layer caudally to the first load-spreading element.

20. The method according to claim 15, wherein:

percutaneously implanting the implant comprises transapically delivering the implant through an apical access point of the heart;

anchoring the caudal end portion to the tissue at the apical region comprises:

positioning the load-spreading element within the ventricle at the apical access point, the load-spreading element being connected to a longitudinal connector;

passing the longitudinal connector through the apical access point; and positioning a locking element adjacent epicardial tissue at the apical access point; and anchoring the caudal end portion to the tissue at the apical region comprises:

moving the locking element along the longitudinal connector toward the load-spreading element; and locking the locking element with respect to the longitudinal connector.

21. The method according to claim 20, wherein the locking element comprises a locking disc.

22. The method according to claim 20, further comprising positioning a sealing layer caudally to the load-spreading element.

* * * * *